United States Patent [19]
Sabatini et al.

[11] Patent Number: 5,966,712
[45] Date of Patent: Oct. 12, 1999

[54] DATABASE AND SYSTEM FOR STORING, COMPARING AND DISPLAYING GENOMIC INFORMATION

[75] Inventors: Cathryn E. Sabatini, San Jose; Joe Don Heath, Sunnyvale; Peter A. Covitz, San Francisco; Tod M. Klingler, Palo Alto; Frank D. Russo, Redwood City; Stephanie F. Berry, Fremont, all of Calif.

[73] Assignee: Incyte Pharmaceuticals, Inc., Palo Alto, Calif.

[21] Appl. No.: 08/857,382

[22] Filed: May 15, 1997

Related U.S. Application Data

[60] Provisional application No. 60/032,565, Dec. 12, 1996.

[51] Int. Cl.$^6$ .................................................. G06F 17/30
[52] U.S. Cl. ............................. 707/104; 707/10; 435/6
[58] Field of Search ................................ 707/104, 10, 6; 435/6

[56] References Cited

U.S. PATENT DOCUMENTS

| | | | |
|---|---|---|---|
| 5,523,208 | 6/1996 | Kohler et al. | 435/6 |
| 5,706,498 | 1/1998 | Fujimiya et al. | 707/6 |
| 5,840,484 | 11/1998 | Seilhamer | 435/6 |

FOREIGN PATENT DOCUMENTS

WO 96/23078  8/1996  WIPO .

OTHER PUBLICATIONS

Keele J. E. et al. "A Conceptual Database Model for Genomic Research" Journal of Computational Biology, vol. 1, No. 1, pp. 65–75, 1994.

Fickett, J. W. finding genes by computer the state of the art, TIG, vol. 12, No. 8. pp. 316–320, Sep. 1996.

National Center for Biotechnology Information; UniGene. Internet—http://www3/ncbi.nlm.nih.gov/unigene (Downloaded Dec. 23, 1997).

National Center for Biotechnology Information; GenBank. Internet—http://www3.ncbi.nlm.nih.gov/web/genbank (Downloaded Dec. 23, 1997).

MAGPIE; Automated Genome Project Investigation Environment. Internet—http://www.mcs.anl.gov/home/gaaster-l.magpie.html (Downloaded Dec. 23, 1997).

Stanford University, Stanford Genomic Resources. Internet—http://genome–www.stanford.edu, Sep. 22, 1996 and Dec. 20, 1997.

Incyte Pharmaceuticals, LIFESEQ Version 4.2 Release Notes and Physical Data Model, Oct. 1996.

Incyte Pharmaceuticals, LIFESEQ Version 3.4 Release Notes, Jan. 1996.

Incyte Pharmaceuticals, LIFESEQ Version 2.5 Release Notes, Jun. 1995.

(List continued on next page.)

*Primary Examiner*—Jack M. Choules
*Attorney, Agent, or Firm*—Beyer & Weaver, LLP

[57] ABSTRACT

Disclosed is a relational database system for storing and manipulating biomolecular sequence information, the database including genomic libraries for a plurality of types of organisms, the libraries having multiple genomic sequences, at least some of which represent open reading frames located along a contiguous sequence on each the plurality of organisms' genomes, and a user interface capable of receiving a selection of two or more of the genomic libraries for comparison and displaying the results of the comparison. The system also provides a user interface capable of receiving a selection of one or more probe open reading frames for use in determining homologous matches between such probe open reading frame(s) and the open reading frames in the genomic libraries, and displaying the results of the determination.

44 Claims, 41 Drawing Sheets

OTHER PUBLICATIONS

Incyte Pharmaceuticals, LIFESEQ Version 3.0 Release Notes, Sep. 1995.

Incyte Pharmaceuticals, LIFESEQ Version 4.0 Release Notes, Apr. 1996.

Incyte Pharmaceuticals, *Introduction to the LIFESEQ Database*, Version 3.4, Jan. 1996.

Incyte Pharmaceuticals, *LIFESEQ Training Manual*, Version 4.1, Jul. 1996.

Matsubara, et al., "Identification of New Genes by Systematic Analysis of cDNAs and Database Construction", *Current Opinion in Biology*, vol. 4, pp. 672–677 (1993).

Lew, K., "GDB 6.0 Goals", http://gbd.gbdnet.ad.jp/gdb/docs/gdb6–goals.html., pp. 1–5 (Mar. 3, 1996).

The Institute for Genomic Research, TIGR Database. Internet—http://www.tigr.org (Downloaded Dec. 23, 1997).

National Center for Biotechnology Information (Index). Internet—http://www3.ncbi.nlm.nih.gov/ (Downloaded Dec. 23, 1997).

National Center for Biotechnology Information; ENTREZ. Internet—http://www3.ncbi.nlm.nih.gov/entrez (Downloaded Dec. 23, 1997).

Green, et al., "Ancient Conserved Regions in New Gene Sequences and the Protein Databases", *Science*, v. 259, n. 5102, pp. 1711–1716 (1993).

http://wehih.wehi.edu.au/ (1995).

Waldrop, et al., "On–line Archives Let Biologists Interrogate the Genome", *Science*, v. 269, n. 5229, pp. 1356–1358 (1995).

No Author, "Incyte Serves Up Information, part I", *In Vivo the Business & Medicine Report*, p. 32, ISSN: 0258–851X (1996).

Martin, et al., "Accessing Genetics Databases", *Database*, v. 17, n. 1, p. 51(8) (1994).

Kanehisa, M. "Toward Pathway Engineering: A New Database Old Genetic and Molecular Pathways." Science and Technology Japan, 1995, No. 59, pp. 34–38.

Gaasterland, T. and Sensen, C. "Using Multiple Tools for Automated Genome Interpretation in a Integrated Environment", Trends In Genetics, Jan. 1996.

Adams, M.D. et al. "Complementary DNA Sequencing: Expressed Sequence Tags and Human Genome Project", Science, Jun. 21, 1991, vol. 252, pp. 1651–1656.

International Search Report for PCT/US97/22691 filed Dec. 11, 1997, Dated Aug. 18, 1998.

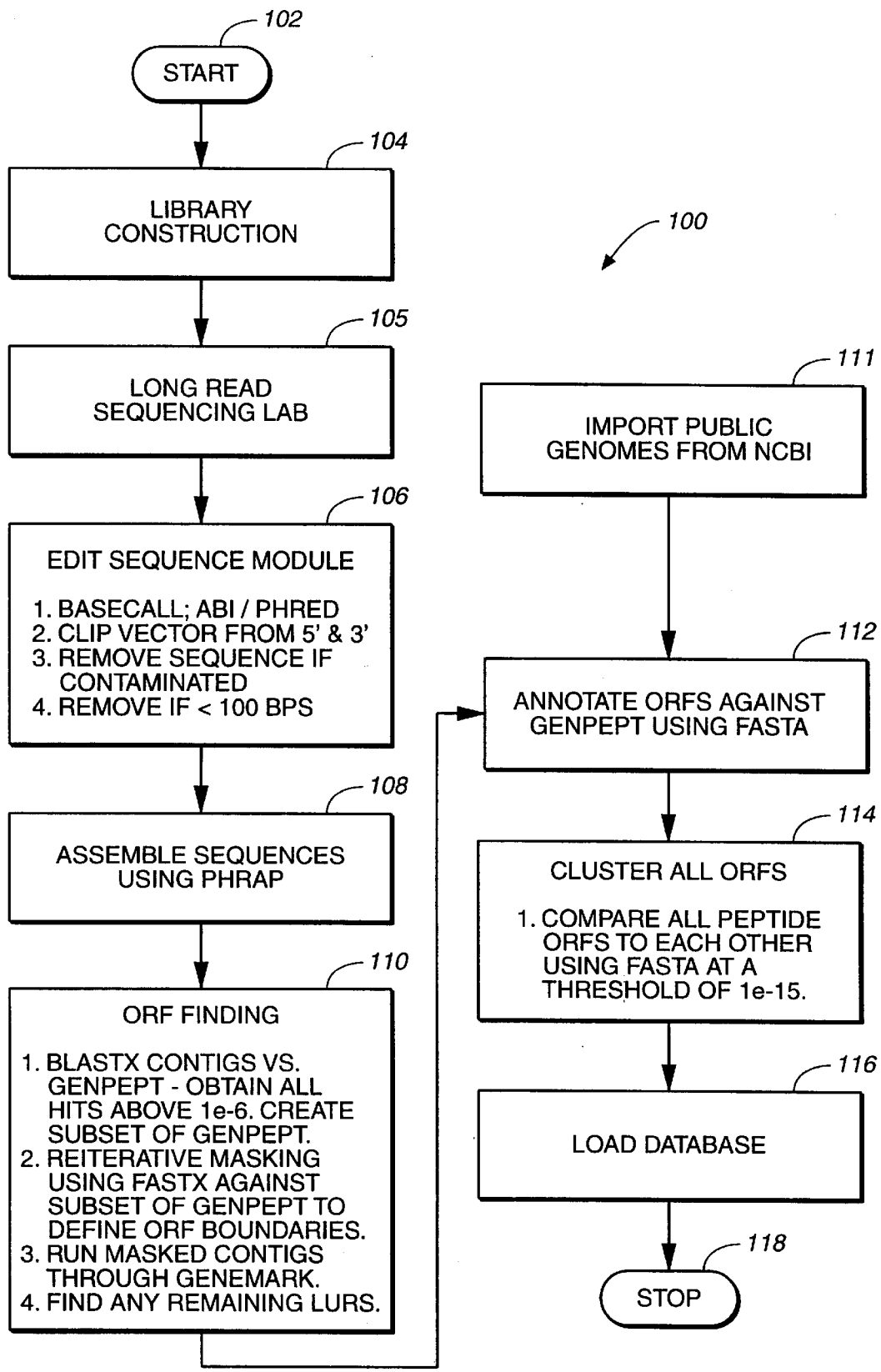
FIG._1

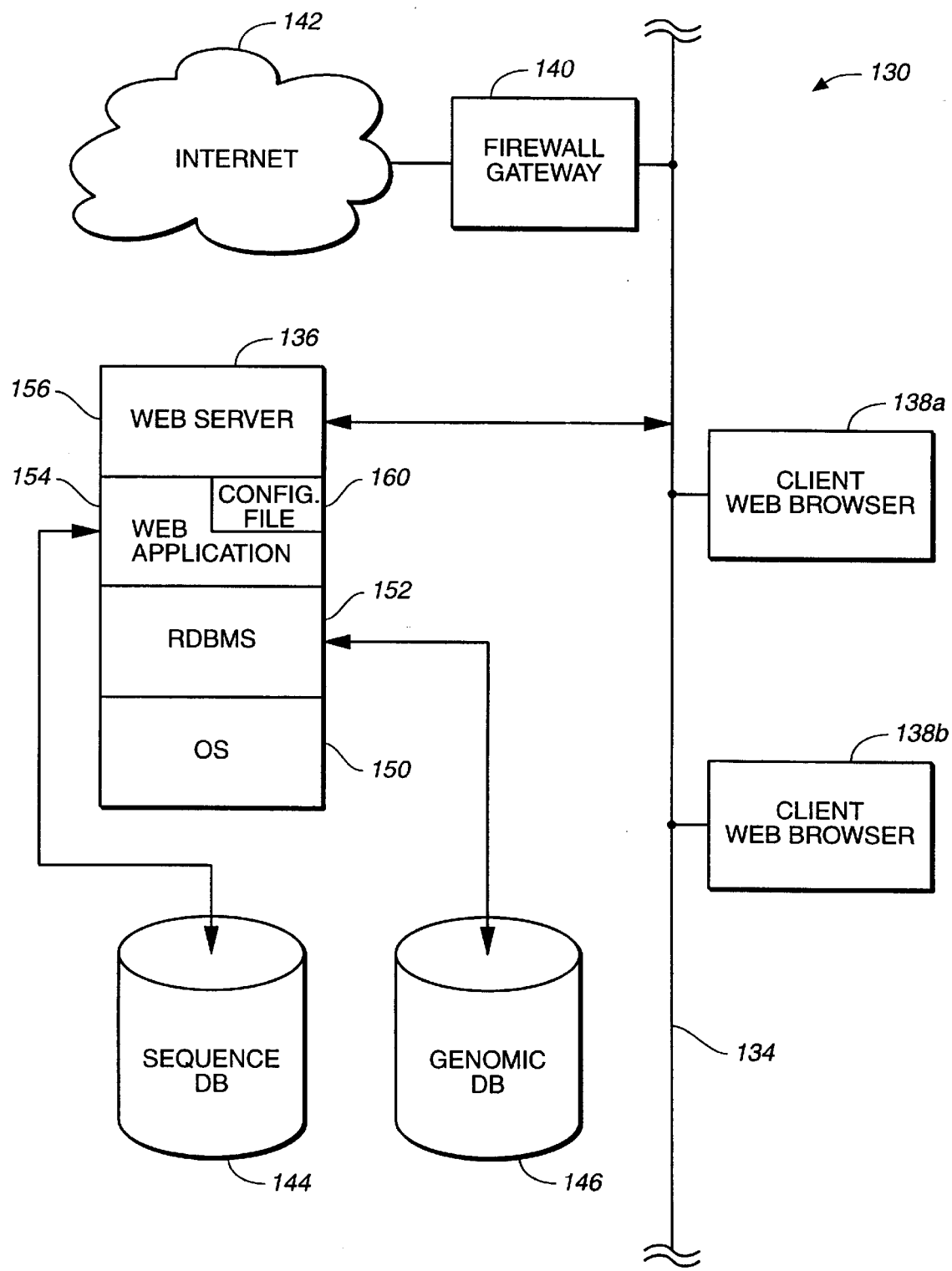
FIG._2A

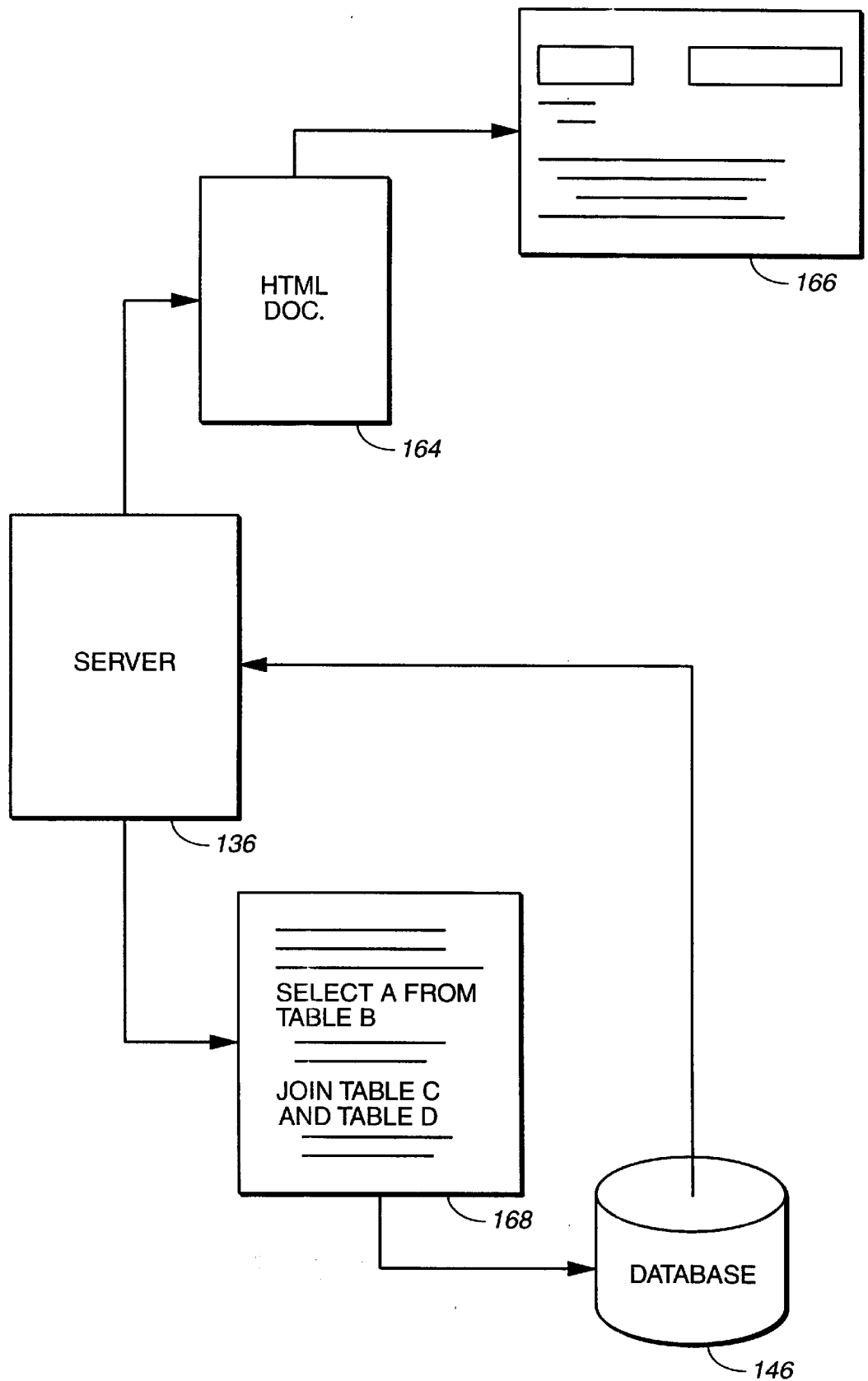
FIG._2B

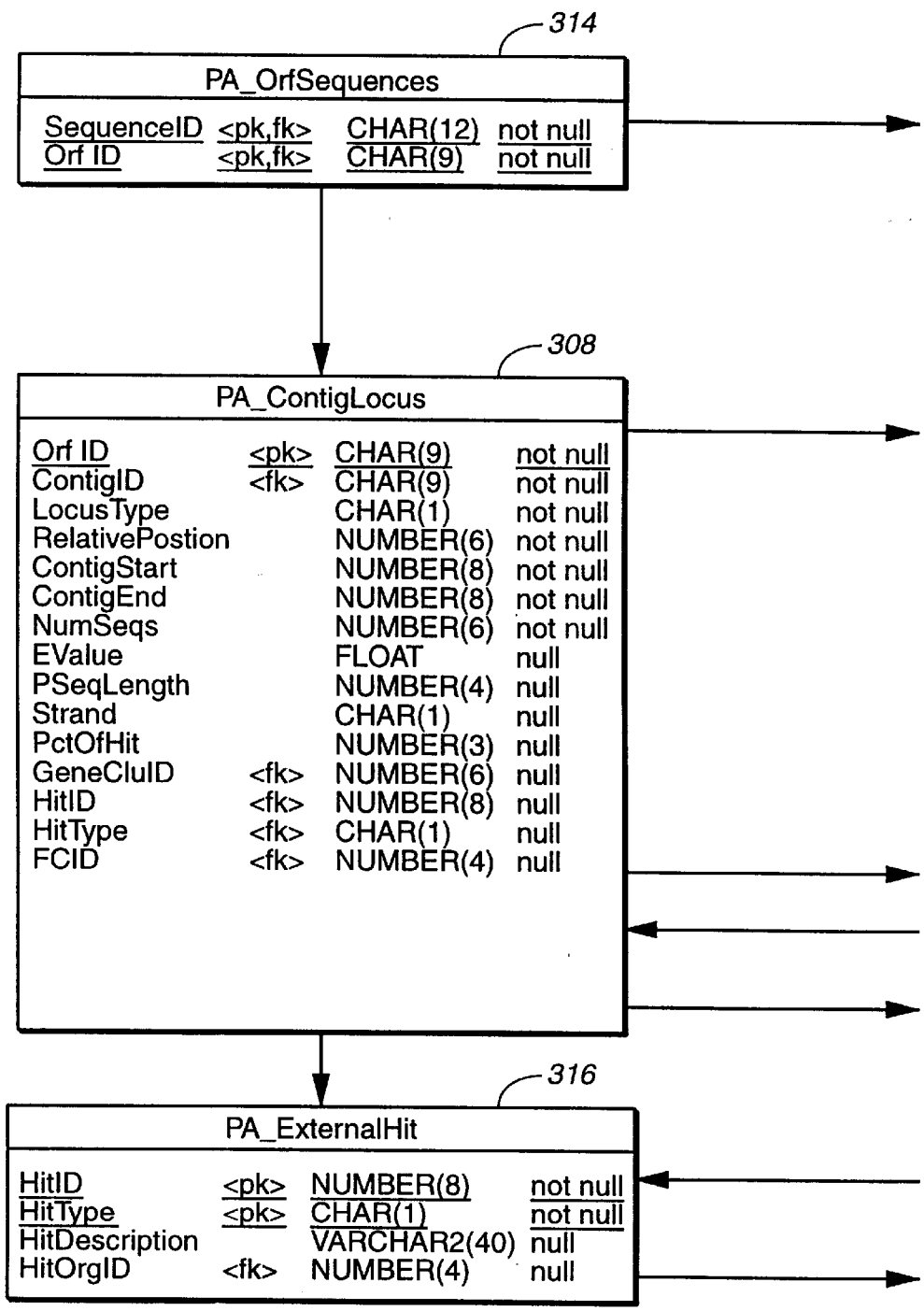
FIG._3A

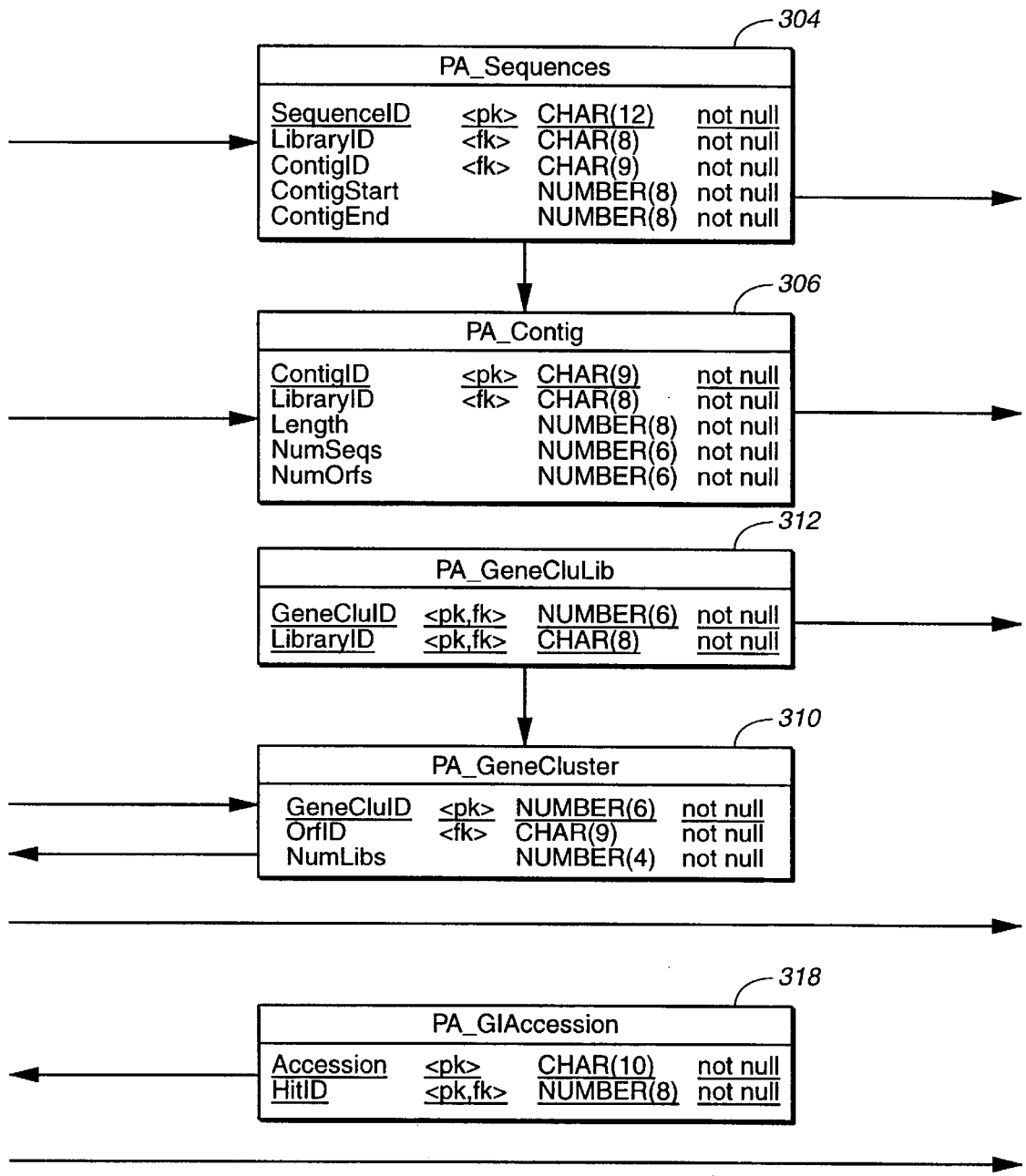
FIG._3B

324

| PA_Version | | | |
|---|---|---|---|
| Software_Product | <pk> | VARCHAR2(20) | not null |
| Software_Version | | VARCHAR2(15) | not null |
| DataRelMonthYear | | VARCHAR2(10) | not null |

302

| PA_Library | | | |
|---|---|---|---|
| LibraryID | <pk> | CHAR(8) | not null |
| OrganismID | | CHAR(8) | not null |
| PctGCContent | | NUMBER(3,1) | not null |
| HitDataSource | | CHAR(12) | not null |
| ContigInSeqServer | | CHAR(1) | not null |
| NumSeqs | | NUMBER(6) | not null |
| NumOrfs | | NUMBER(6) | not null |
| NumContigs | | NUMBER(6) | not null |
| OrphanContigs | | NUMBER(6) | not null |
| LibDescription | | VARCHAR2(40) | not null |
| Comments | | VARCHAR2(1000) | not null |
| Genome Size | | NUMBER(4,2) | null |
| Depth | | NUMBER(3,1) | null |
| Coverage | | NUMBER(3) | null |

322

| PA_FuncClass | | | |
|---|---|---|---|
| FCID | <pk> | NUMBER(4) | not null |
| Name | | VARCHAR2(30) | not null |
| SortOrder | | NUMBER(4) | not null |

320

| PA_HitOrganism | | | |
|---|---|---|---|
| HitOrgID | <pk> | NUMBER(4) | not null |
| HitOrganism | | VARCHAR2(25) | not null |

*FIG._3C*

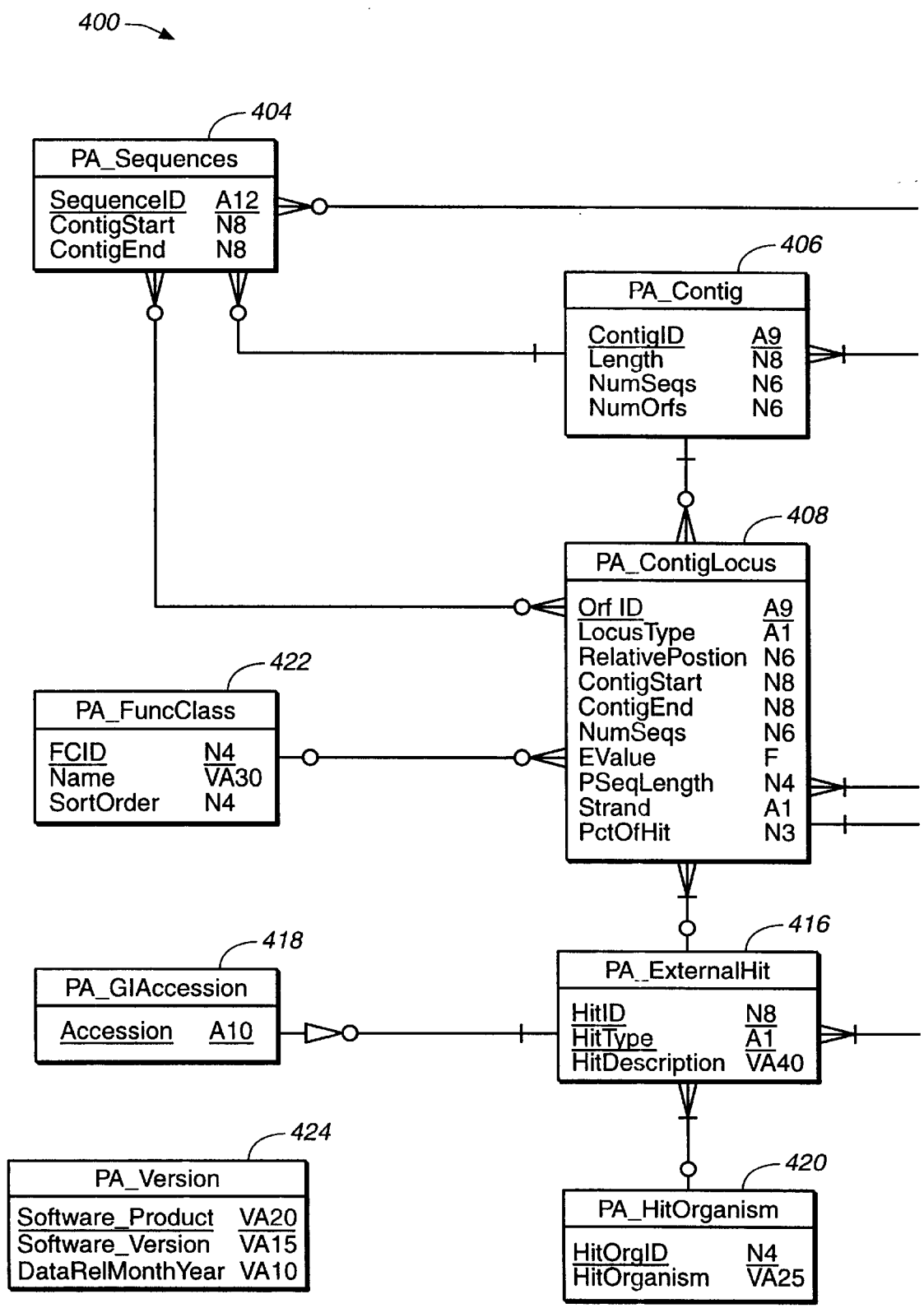
FIG._4A

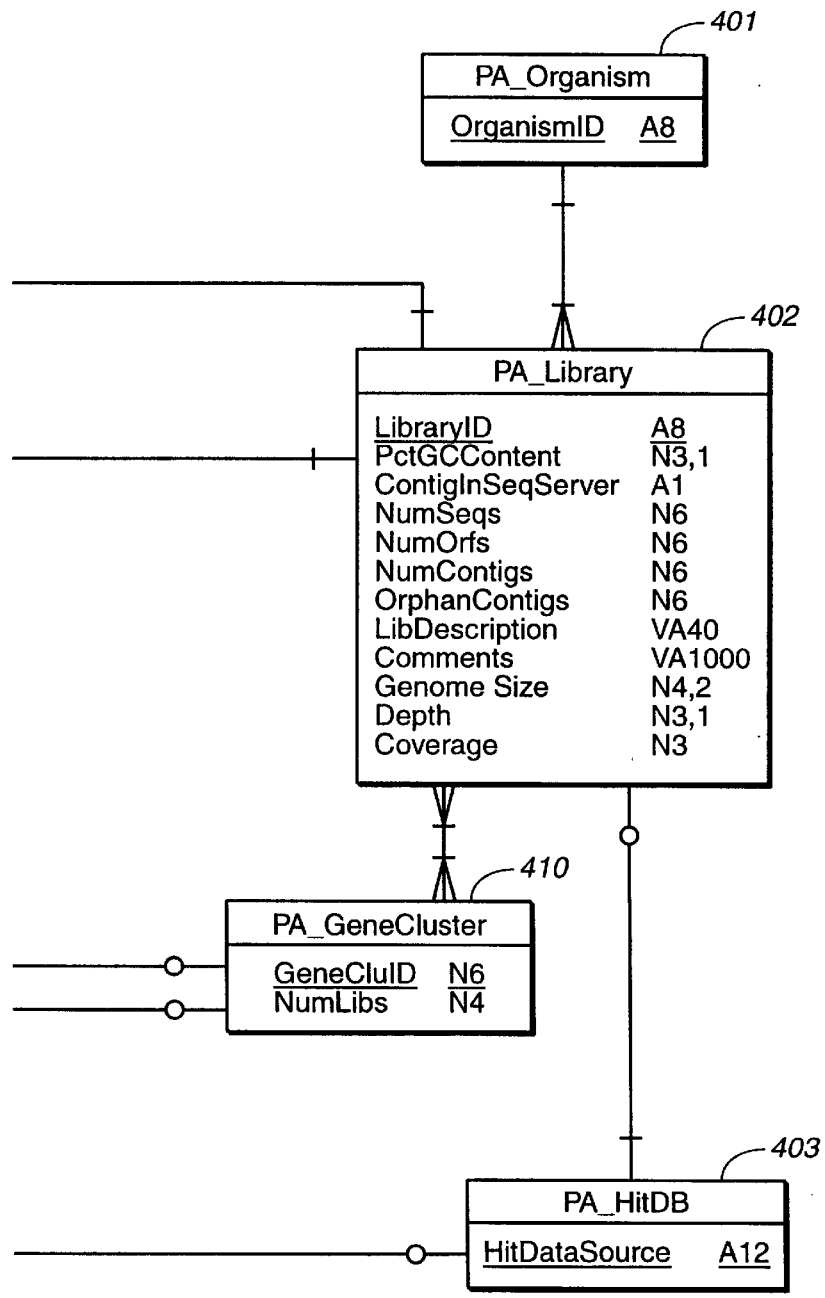
FIG._4B
FIG._4

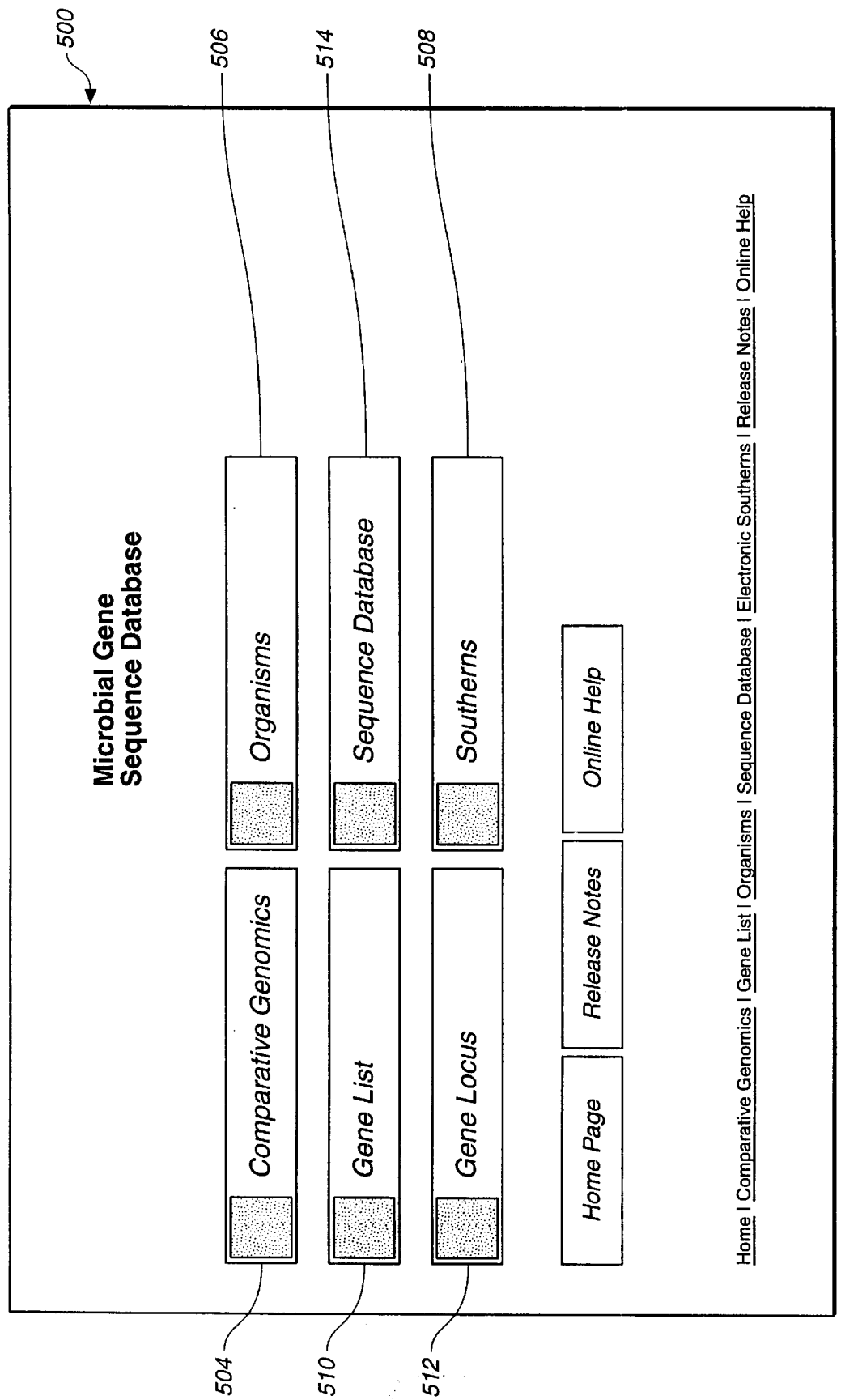
FIG._5A

Organism Information Results

| Main Menu | Comparisons | Gene List | Gene Locus | Org Info | Sequences | Southerns | Help |

| Library | Description | Usable | Contigs | ORFs | Aprx Size | Depth | Coverage | GC Content |
|---|---|---|---|---|---|---|---|---|
| ECOLI01 | Escherichia coli (4.6Mbp) | N/A | 1 | 3511 | 4.6 Mbp | N/A | 100% | 51.0% |
| EFAECA01 | Enterococcus faecalis (2.8Mbp) | 20798 | 1449 | 2625 | 2.8 Mbp | 4.0 | 94% | 38.0% |
| HINFLU01 | Haemophilus influenzae (1.8Mbp) | N/A | 1 | 1673 | 1.8 Mbp | N/A | 100% | 38.0% |
| MGENIT01 | Mycoplasma genitalium (0.7Mbp) | N/A | 1 | 467 | 0.7 Mbp | N/A | 100% | 32.0% |
| MJANNA01 | Methanococcus jannaschii (1.7Mbp) | N/A | 1 | 1674 | 1.7 Mbp | N/A | 100% | 31.0% |
| MPNEUM01 | Mycoplasma pneumoniae (0.8Mbp) | N/A | 1 | 678 | 0.8 Mbp | N/A | 100% | 40.0% |
| SAUREU01 | Staphylococcus aureus (2.8Mbp) | 27704 | 1050 | 2206 | 2.8 Mbp | 5.7 | 88% | 34.0% |
| SEPIDE01 | Staphylococcus epidermidis (2.4Mbp) | 27538 | 485 | 2195 | 2.4 Mbp | 6.4 | 105% | 32.0% |
| SPYOGE01 | Streptococcus pyogenes (2.0Mbp) | 15263 | 1102 | 2049 | 2.0 Mbp | 4.3 | 100% | 39.0% |
| SPYOGE02 | Streptococcus pyogenes (2.0Mbp) | N/A | 194 | 1381 | 2.0 Mbp | N/A | N/A | 39.0% |
| SYNECH01 | Synechocystis sp. (3.6Mbp) | N/A | 1 | 3169 | 3.6 Mbp | N/A | 100% | 48.0% |

Organism Information Results returned a total of 11 row(s).

FIG._5B

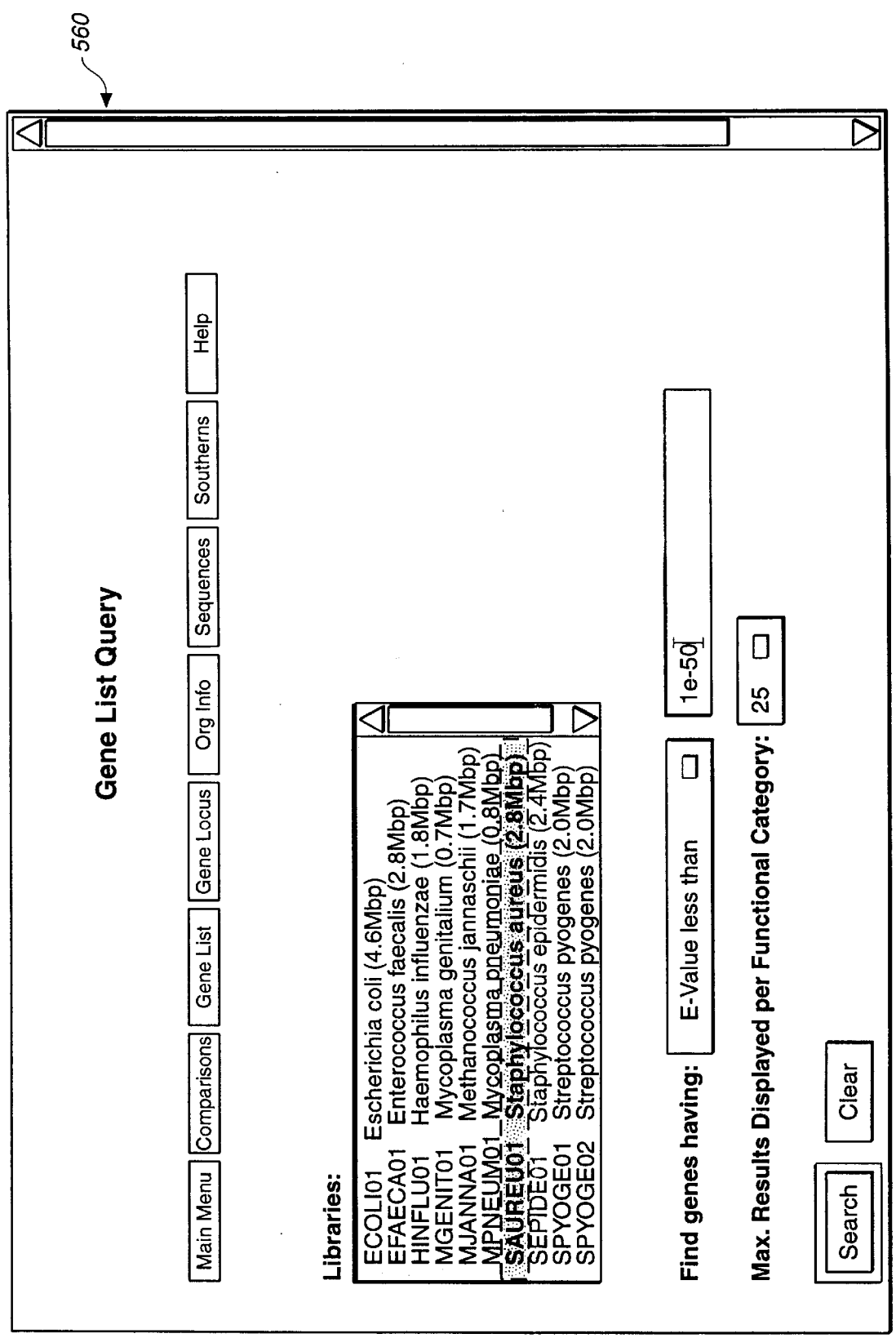
FIG._5C

Gene List Results

| Main Menu | Comparisons | Gene List | Gene Locus | Org Info | Sequences | Southerns | Help |

E-Values less than 1e-50

Library: SAUREU01     HitDataSource: pagenpept98     Orphan Contigs: 250     Total Contigs: 1050

Virulence

| ORF ID | Hit ID | Hit Description | Hit Organism | E-Value | NumLibs (11) | ORF Coverage |
|---|---|---|---|---|---|---|
| SAU101050 | gi1657640 | Cap8A | Staphylococcus | 0 | 1 | 100% |
| SAU101051 | gi1657641 | Cap8B | Staphylococcus | 0 | 2 | 100% |
| SAU101052 | gi1657642 | Cap8C | Staphylococcus | 0 | 1 | 100% |
| SAU101053 | gi1657643 | Cap8D | Staphylococcus | 0 | 2 | 100% |
| SAU101054 | gi1657644 | Cap8E | Staphylococcus | 0 | 2 | 99% |
| SAU102369 | gi1657645 | Cap8F | Staphylococcus | 0 | 1 | 45% |
| SAU100018 | gi1657646 | Cap8G | Staphylococcus | 0 | 1 | 52% |
| SAU100044 | gi1657647 | Cap8H | Staphylococcus | 0 | 1 | 58% |
| SAU102352 | gi1657648 | Cap8I | Staphylococcus | 0 | 1 | 42% |
| SAU102470 | gi1657649 | Cap8J | Staphylococcus | 0 | 1 | 50% |
| SAU101562 | gi1657650 | Cap8K | Staphylococcus | 0 | 1 | 45% |
| SAU101563 | gi1657651 | Cap8L | Staphylococcus | 0 | 2 | 100% |
| SAU101564 | gi1657652 | Cap8M | Staphylococcus | 0 | 4 | 100% |
| SAU101565 | gi1657653 | Cap8N | Staphylococcus | 0 | 1 | 100% |
| SAU101566 | gi1657654 | Cap8O | Staphylococcus | 0 | 6 | 100% |
| SAU101567 | gi1657655 | Cap8P | Staphylococcus | 0 | 6 | 100% |
| SAU100643 | g506697 | CapA | Staphylococcus | 0 | 1 | 99% |

FIG._5D

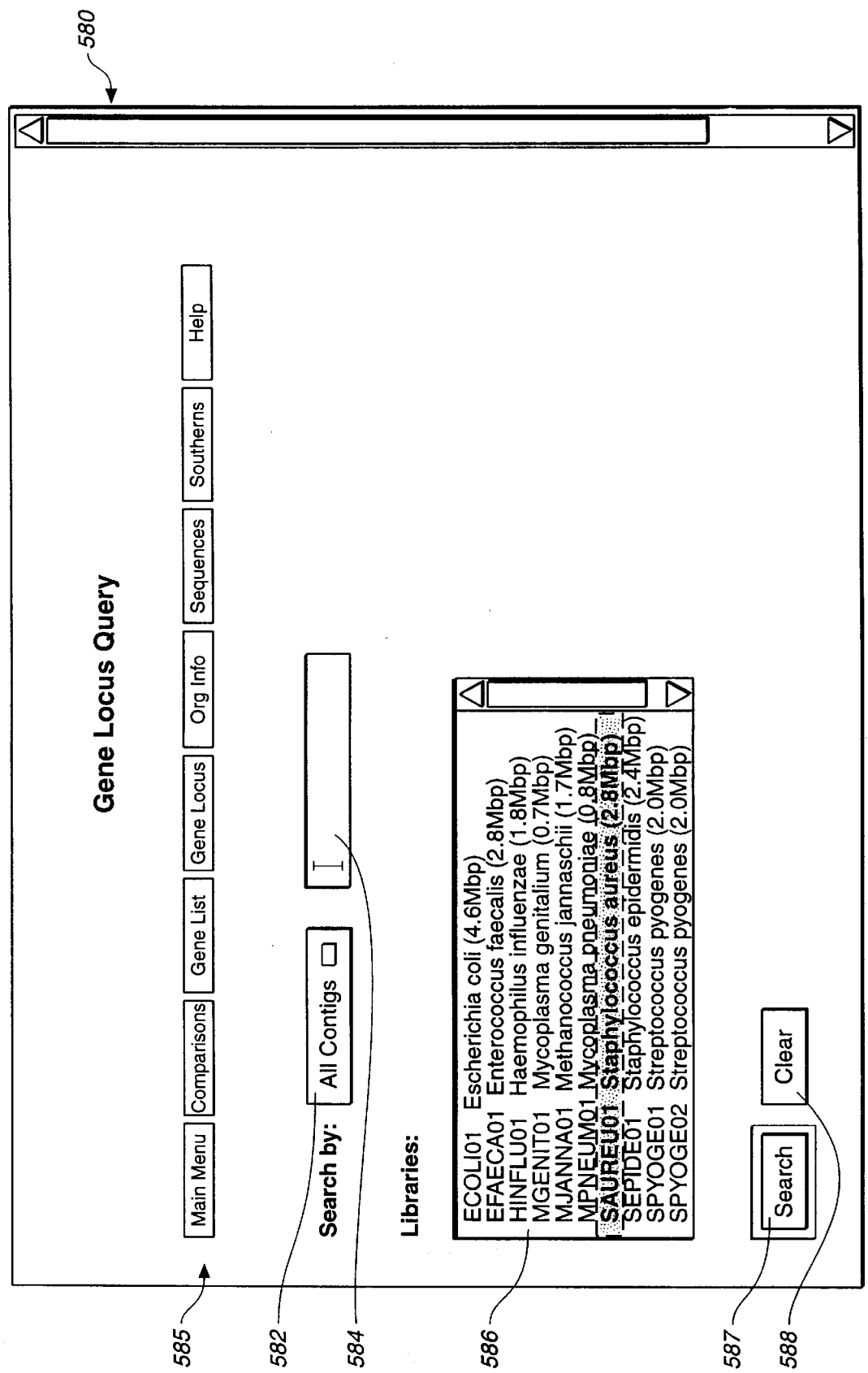
FIG._5E

Gene Locus Results

| Main Menu | Comparisons | Gene List | Gene Locus | Org Info | Sequences | Southerns | Help |

Library: SAUREU01  HitDataSource: pagenpept98  Orphan Contigs: 250  Total Contigs: 1050

Search All Contigs

Contig ID: SAU1c0001   Length: 640   Total seqs: 1

| Orf ID | Hit ID | Hit Description | Hit Organism | E-Value | Strand | Coordinates | NumLibs (11) | NumSeqs |
|---|---|---|---|---|---|---|---|---|
| SAU100001 | g1377829 | unknown | Bacillus subtil | 2.8e-29 | - | 296,640 | 6 | 1 |

Contig ID: SAU1c0003   Length: 728   Total seqs: 1

| Orf ID | Hit ID | Hit Description | Hit Organism | E-Value | Strand | Coordinates | NumLibs (11) | NumSeqs |
|---|---|---|---|---|---|---|---|---|
| SAU100002 | g1652035 | fmu and fmv protein | Synechocystis s | 0 | - | 175,582 | 3 | 1 |

Contig ID: SAU1c0006   Length: 732   Total seqs: 1

| Orf ID | Hit ID | Hit Description | Hit Organism | E-Value | Strand | Coordinates | NumLibs (11) | NumSeqs |
|---|---|---|---|---|---|---|---|---|
| SAU100003 | g467462 | cysteine synthetase A | Bacillus subtil | 2.7e-24 | - | 125,427 | 3 | 1 |

Contig ID: SAU1c0011   Length: 467   Total seqs: 1

| Orf ID | Hit ID | Hit Description | Hit Organism | E-Value | Strand | Coordinates | NumLibs (11) | NumSeqs |
|---|---|---|---|---|---|---|---|---|

FIG._5F

Comparative Genomics Query

Main Menu | Comparisons | Gene List | Gene Locus | Org Info | Sequences | Southerns Help

Target Libraries:
(Look for genes common to all the libraries selected from this list.)

```
ECOLI01   Escherichia coli (4.6Mbp)
EFAECA01  Enterococcus faecalis (2.8Mbp)
HINFLU01  Haemophilus influenzae (1.8Mbp)
MGENIT01  Mycoplasma genitalium (0.7Mbp)
MJANNA01  Methanococcus jannaschii (1.7Mbp)
MPNEUM01  Mycoplasma pneumoniae (0.8Mbp)
SAUREU01  Staphylococcus aureus (2.8Mbp)
```

Background Libraries: (Optional)
(Exclude genes in any of the libraries selected from this list.)

```
ECOLI01   Escherichia coli (4.6Mbp)
EFAECA01  Enterococcus faecalis (2.8Mbp)
HINFLU01  Haemophilus influenzae (1.8Mbp)
MGENIT01  Mycoplasma genitalium (0.7Mbp)
MJANNA01  Methanococcus jannaschii (1.7Mbp)
MPNEUM01  Mycoplasma pneumoniae (0.8Mbp)
SAUREU01  Staphylococcus aureus (2.8Mbp)
```

Max. Results Displayed: ALL ☐

*FIG._6A*

Comparative Genomics Results

| Main Menu | Comparisons | Gene List | Gene Locus | Org Info | Sequences | Southerns | Help |

Target Library: SAUREU01

Background Library: EFAECA01, HINFLU01

| Hit ID | Hit Description | Hit Organism | E-Value | NumLibs (11) |
|---|---|---|---|---|
| g1306 | ultra high-sulphur keratin protein | Ovis aries | 0 | 1 |
| g7174 | coding region (AA 448) | Dictyostelium d | 7.8e-07 | 2 |
| g39656 | spoVG gene product | Bacillus megate | 6.6e-24 | 1 |
| g39782 | 33kDa lipoprotein | Bacillus subtil | 2.4e-09 | 1 |
| g39813 | phospho-2-dehydro-3-deoxyheptonate aldo | Bacillus subtil | 5.7e-10 | 2 |
| g39815 | orf 2 gene product | Bacillus subtil | 3.2e-14 | 2 |
| g40174 | ORF X | Bacillus subtil | 3.5e-13 | 2 |
| g40896 | aconitate hydratase | Escherichia col | 0 | 3 |
| g41587 | glycerol-3-phosphatase transporter (AA | Escherichia col | 0 | 5 |
| g41731 | HMP haemoprotein | Escherichia col | 0 | 3 |
| g41750 | hsdR protein (AA 1-1033) | Escherichia col | 4.7e-20 | 1 |
| g41996 | unidentified ORF (269 AA) | Escherichia col | 0 | 3 |
| g42009 | moaB gene product | Escherichia col | 0 | 4 |
| g42086 | nitrate reductase alpha subunit | Escherichia col | 0 | 3 |
| g44076 | ribosomal protein B | Lactococcus lac | 1.9e-20 | 6 |
| g46491 | SmtB | Synechococcus P | 4.5e-10 | 2 |
| g46512 | orf 7 | Staphylococcus | 0 | 3 |
| g46589 | ORF 2 (68 AA) (2187 is 2nd base in codo | Staphylococcus | 1.5e-16 | 1 |
| g46591 | Sphingomyelinase | Staphylococcus | 2.4e-21 | 1 |
| g46687 | preproenzyme (AA -68 to 268) | Staphylococcus | 0 | 2 |
| g46687 | preproenzyme (AA -68 to 268) | Staphylococcus | 1.5e-07 | 1 |

FIG._6B

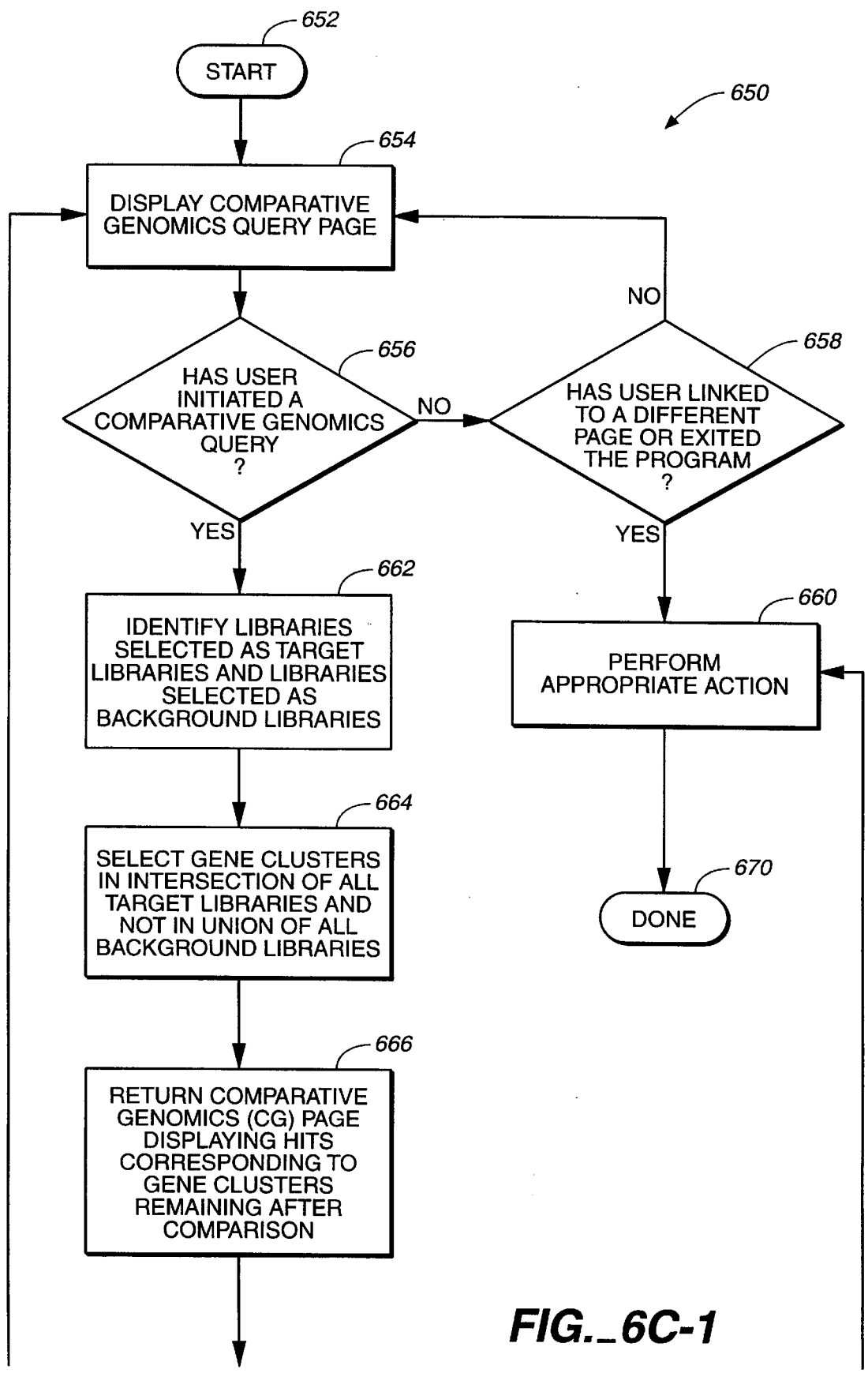
FIG._6C-1

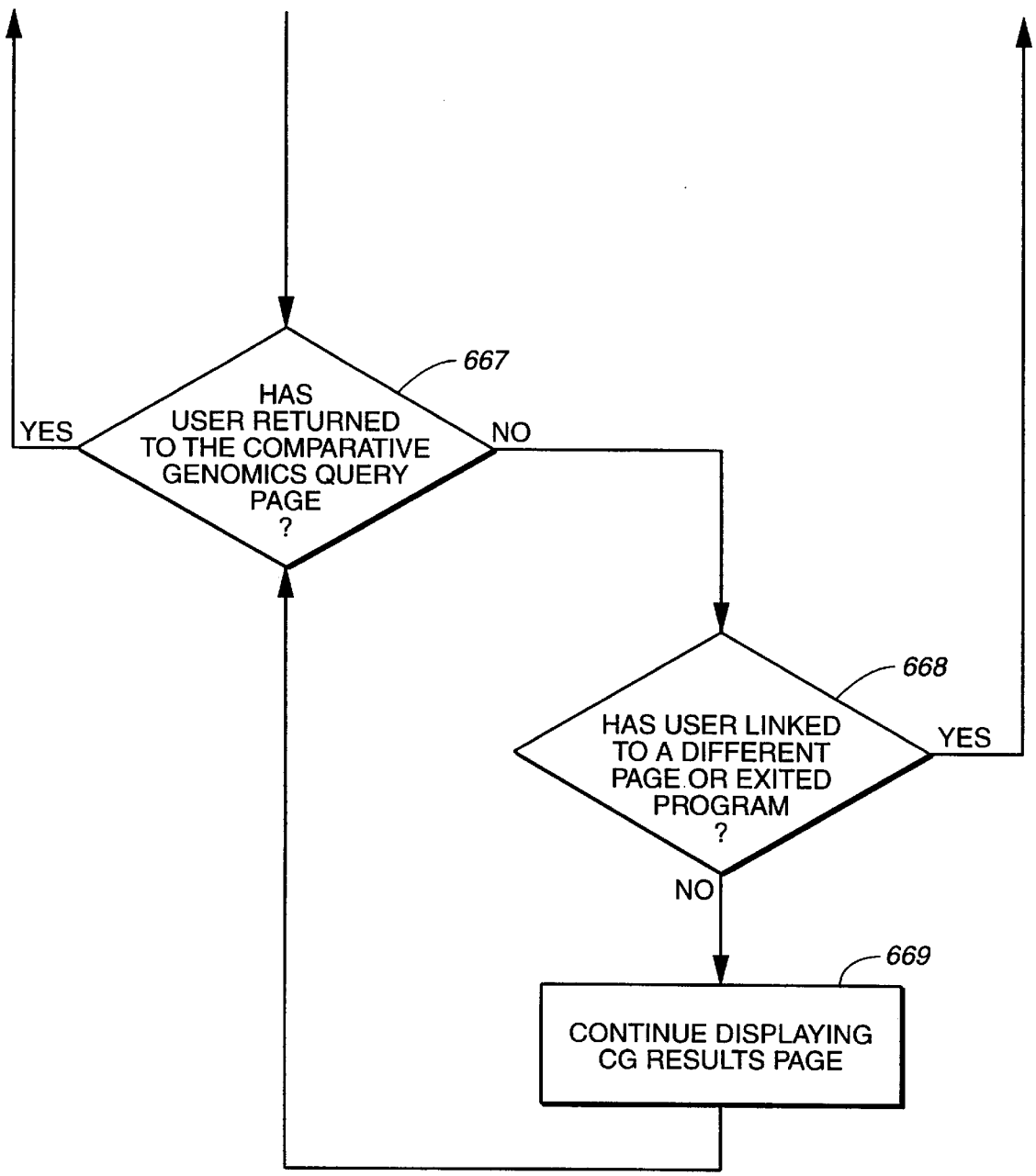
FIG._6C-2
FIG._6C

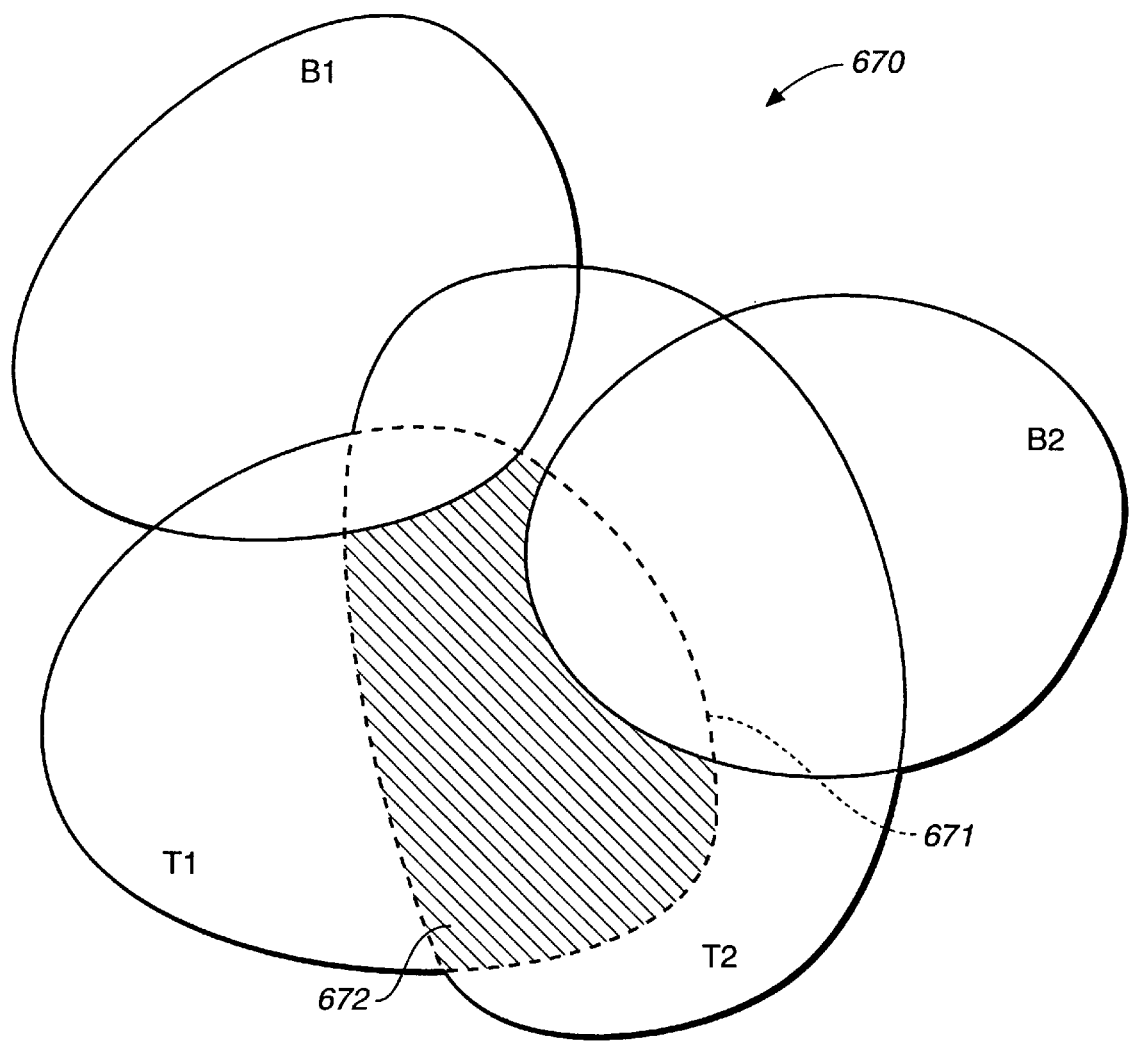
FIG._6D

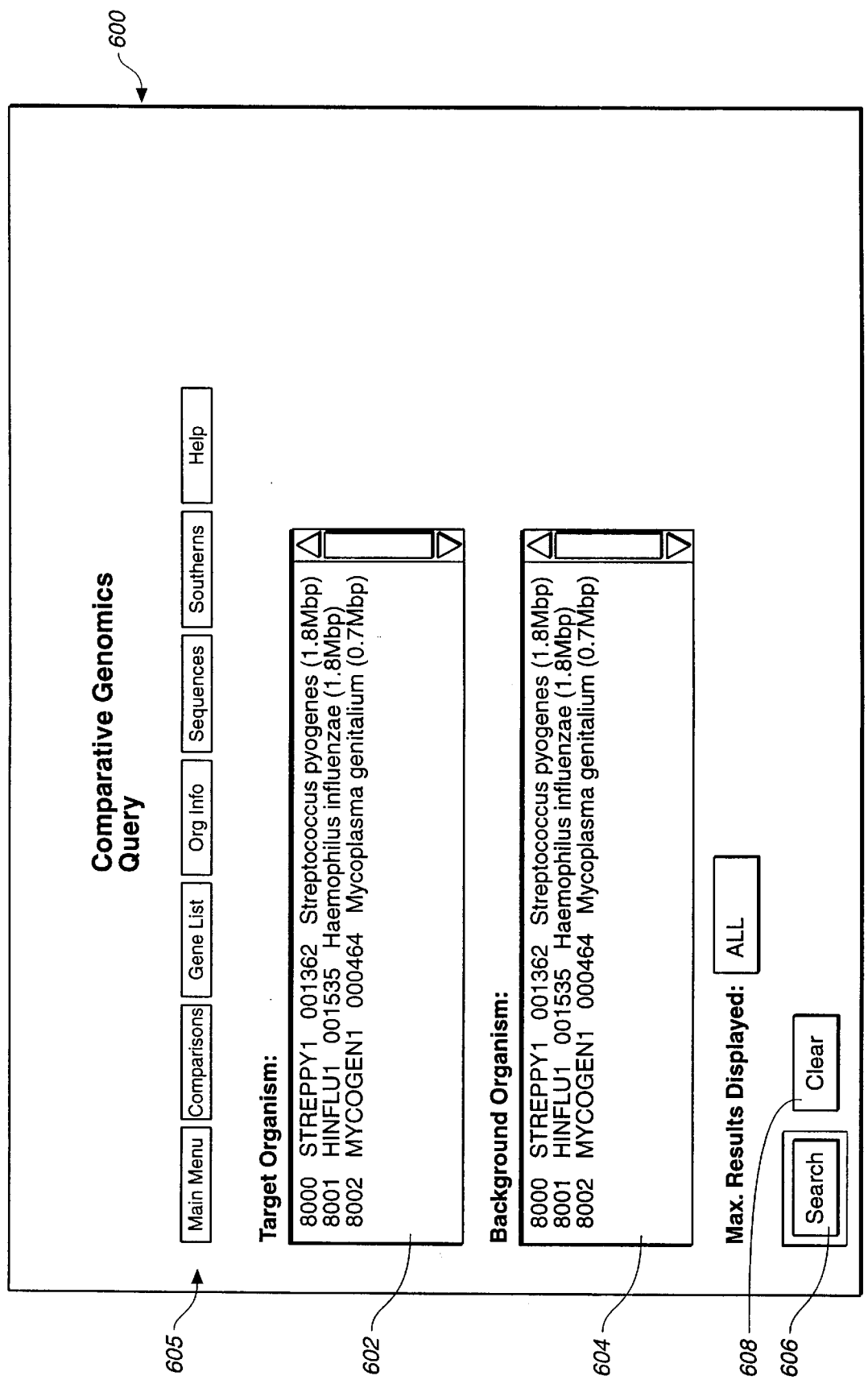
FIG._6E

| | | | |
|---|---|---|---|
| g849022 | Lactate oxidase | gb97bctp | 4.9e-82 0.6667 |
| g853775 | unknown | gb97bctp | 1.6e-25 0.6667 |
| g881507 | hyaluronidase | gb97bctp | 0 0.6667 |
| g882579 | CG Site No. 29739 | gb97bctp | 1.1e-41 0.6667 |
| g887862 | internalin | gb97bctp | 3.9e-25 0.6667 |
| g897793 | y98 gene product | gb97bctp | 2.8e-22 0.6667 |
| N | | | |
| g1591153 | hypothetical protein (SP:P46348) | gb97bctp | 4.5e-31 0.6667 |
| g1591731 | melvalonate kinase | gb97bctp | 4.1e-14 0.6667 |
| g1591838 | hypothetical protein (PIR:S21569) | gb97bctp | 1.4e-41 0.6667 |
| g1591853 | M. jannaschii predicted coding region MJ | gb97bctp | 5.6e-13 0.6667 |
| g1592030 | M. jannaschii predicted coding region MJ | gb97bctp | 1.7e-17 0.6667 |
| g1592085 | M. jannaschii predicted coding region MJ | gb97bctp | 1.6e-08 0.6667 |
| g1592823 | beta-galactosidase | gb97bctp | 1.2e-20 0.6667 |
| g1617437 | histidine kinase | gb97bctp | 1.6e-29 0.6667 |
| g1617438 | response regulator | gb97bctp | 2.8e-43 0.6667 |
| g1619837 | collagen-like protein | gb97bctp | 1.1e-64 0.6667 |

Comparative Genomics Results returned a total of 317 row(s).

| FIG._6F-1 |
|---|
| FIG._6F-2 |

Electronic Southern Results

[Main Menu] [Comparisons] [Gene List] [Org Info] [Sequences] [Southerns] [Help]

The Electronic Southern for the ORF ID: SP001074

| Library | Library Description | Copies | ORF ID |
|---|---|---|---|
| STREPPY1 | Streptococcus pyogenes (1.8Mbp) | 1 | SP001074 |

Electronic Southern Results returned a total of 1 row(s).

FIG._6G

Organism Gene Copies

[Main Menu] [Comparisons] [Gene List] [Org Info] [Sequences] [Southerns] [Help]

Library: STREPPY1

| Orf ID | Hit ID | Hit Description | DataSource | P-Value |
|---|---|---|---|---|
| SP001074 | g144861 | hyaluronidase | gb97bctp | 2.3e-12 |

Organism Gene Copies returned a total of 1 row(s).

FIG._6H

Gene Locus Information

| Main Menu | Comparisons | Gene List | Org Info | Sequences | Southerns | Help |

Library: STREPPY1
Hit ID: g144861    Hit description: hyaluronidase

Contig ID: SPc00596    Length: 5801    Total Seqs: 49

| Orf ID | Hit ID | Hit Description | Hit DataSource | P-Value |
|---|---|---|---|---|
| SP001072 | g149205 | histidine utilization repressor C (hutC) | gb97bctp | 3.2e-08 |
| SP001073 | g289864 | regulatory protein | gb97bctp | 5.7e-12 |
| *SP001074* | *g144861* | *hyaluronidase* | *gb97bctp* | *2.3e-12* |
| LUR | | | | 1 |
| SP001076 | g40665 | beta-glucosidase | gb97bctp | 3.2e-82 |
| LUR | | | | 1 |
| SP001078 | g1001409 | hypothetical protein | gb97bctp | 1.7e-23 |

Gene Locus Information Results returned a total of 7 row(s).

BLAST Search Results

| Main Menu | Comparisons | Gene List | Org Info | Sequences | Southerns | Help |

BLASTX 1.4.8MP-WashU [1-Jun-95] [Build 11:49:05 Nov 8 1995]

Reference: Gish, Warren and David J. States (1993). Identification of protein coding regions by database similarity search. Nat. Genet. 3:266-72. Altschul, Stephen F., Warren Gish, Webb Miller, Eugene W. Myers, and David J. Lipman (1990). Basic local alignment search tool. J. Mol. Biol. 215:403-10.

Notice: statistical significance is estimated under the assumption that the equivalent of one entire reading frame in the query sequence codes for protein and that significant alignments will involve only coding reading frames.

Query= SPc00596
       (5671 letters)

Translating both strands of query sequence in all 6 reading frames

Database: /tmp/baaaaebva
          1 sequences; 1042 total letters.
Searching done Sequences producing High-scoring Segment Pairs:

|  | Reading Frame | High Score | Smallest Sum Probability P(N) | N |
|---|---|---|---|---|
| g144861 nagH; hyaluronidase | +3 | 141 | 4.2e-18 | 6 |

FIG. 6J-2

>g144861    nagH; hyaluronidase
Length = 1042

Plus Strand HSPs:

Score = 141 (64.6 bits), Expect = 2.7e-17, Sum P(5) = 2.7e-17
Identities = 25/77 (32%), Positives = 45/77 (58%), Frame = +3

Query:   1419  G*LKAFMEHRGXREERIDCLRFIGNKRMNTYMYAPKDDDYQRKLWRDLYPEDWTYFKEL 1598
               G  ++ +    E+R + +++F G+ ++N Y+++APKDD Y   WRDLYPE+ ++ K+L
Sbjct:   188   GFIEGYYGNPWSNEDRAELMKFGGDYKLNQYVFAPKDDPYHNSKWRDLYPEEKLSEIKKL 247

Query:   1599  LAVAKEEGIDFWYMISP 1649
               + E   + Y + P
Sbjct:   248   AQMGNETKNRYVYALHP 264

Score = 63 (28.9 bits), Expect = 1.7e-07, Sum P(5) = 1.7e-07
Identities = 11/23 (47%), Positives = 12/23 (52%), Frame = +2

Query:   1415  RGIIEGFYGTPWXTRGTNRLPTF 1483
               RG IEG+YG PW      L  F
Sbjct:   187   RGFIEGYYGNPWSNEDRAELMKF 209

Score = 54 (24.7 bits), Expect = 2.7e-17, Sum P(5) = 2.7e-17
Identities = 11/29 (37%), Positives = 17/29 (58%), Frame = +3

Query:   2154  QVKGIVSNPMISWELSKLTLTDMSHYLWD 2240
               ++ GIV NPM   E +K  L ++ Y W+
Sbjct:   436   KIDGIVLNPMQQAEANKSALFAIADYAWN 464

Score = 47 (21.5 bits), Expect = 2.7e-17, Sum P(5) = 2.7e-17
Identities = 8/23 (34%), Positives = 16/23 (69%), Frame = +3

FIG._6J-3

```
Query:  1872 ELVICPTEYDNHHDSIYLQELSE 1940
             +L+ CP++Y  +  S  L+EL++
Sbjct:   341 DLMFCPSDYYGNGSSAQLKELNK 363

Score = 47 (21.5 bits), Expect = 1.3e-05, Sum P(5) = 1.3e-05
Identities = 8/23 (34%), Positives = 14/23 (60%), Frame = +3

Query:  153 SPEANKDLLLILPFASDYELGDY 221
            +P +N+D    ++ F  DY+L Y
Sbjct:  196 NPWSNEDRAELMKFGGDYKLNQY 218

Score = 43 (19.7 bits), Expect = 2.7e-17, Sum P(5) = 2.7e-17
Identities = 11/34 (32%), Positives = 16/34 (47%), Frame = +3

Query: 1656 DFDYTKEEDYQLLYQKLQQLLALGVCHFGLLLDD 1757
            D +   + D  ++ K  QLL   V  F +L DD
Sbjct:  273 DTEENYQNDLGVIKAKFTQLLENDVRQFAILADD 306

Score = 37 (17.0 bits), Expect = 4.2e-18, Sum P(6) = 4.2e-18
Identities = 9/27 (33%), Positives = 11/27 (40%), Frame = +2

Query: 3200 GDRVKDWFVHNEPMVVEGSYLMQFHY 3280
            GD    W  ++E      S    FHY
Sbjct:  600 GDDEAAWANYSEAQSAFEKSKTYGFHY 626

Score = 37 (17.0 bits), Expect = 2.7e-17, Sum P(5) = 2.7e-17
Identities = 5/21 (23%), Positives = 11/21 (52%), Frame = +2

Query: 4280 ISLEGVGICRTRYKRSVWFGI 4342
            + +  GV +  T  + + W G+
Sbjct:  769 LKVRGVRLIATEARENTWLGV 789

Score = 37 (17.0 bits), Expect = 1.5e-14, Sum P(4) = 1.5e-14
Identities = 4/5 (80%), Positives = 5/5 (100%), Frame = +1

Query: 5602 WLNWP 5616
            W+NWP
Sbjct:  406 WINWP 410
```

FIG._6J-4

Score = 36 (16.5 bits), Expect = 3.8e-12, Sum P(3) = 3.8e-12, Frame = +2
Identities = 7/19 (36%), Positives = 12/19 (63%), Frame = +2

Query:   3437  QSEADMAAAHFTELWNNDL  3493
               Q++    + A FT+L ND+
Sbjct:    279  QNDLGVIKAKFTQLLENDV  297

Score = 35 (16.0 bits), Expect = 0.0076, Sum P(4) = 0.0076, Frame = +1
Identities = 4/5 (80%), Positives = 4/5 (80%), Frame = +1

Query:   268  WFNWP  282
              W NWP
Sbjct:   406  WINWP  410

Minus Strand HSPs:

Score = 43 (19.7 bits), Expect = 3.1, P = 0.95, Frame = -2
Identities = 7/16 (43%), Positives = 11/16 (68%), Frame = -2

Query:   720  TNRFPRQAPF*WLSFP  673
              T   P +APF W+++P
Sbjct:   395  TEGHPGRAPFFWINWP  410

Parameters:

V=500
B=250
-ctxfactor=6.00
E=10

| Query Frame | MatID | Matrix name | Lambda | As Used K | H | Lambda | Computed K | H |
|---|---|---|---|---|---|---|---|---|
| Std. | 0 | BLOSUM62 | 0.318 | 0.135 | 0.401 | 0.318 | 0.135 | 0.401 |
| +3 | 0 | BLOSUM62 | 0.318 | 0.135 | 0.401 | 0.343 | 0.151 | 0.492 |
| +2 | 0 | BLOSUM62 | 0.318 | 0.135 | 0.401 | 0.352 | 0.158 | 0.572 |
| +1 | 0 | BLOSUM62 | 0.318 | 0.135 | 0.401 | 0.362 | 0.161 | 0.612 |
| -1 | 0 | BLOSUM62 | 0.318 | 0.135 | 0.401 | 0.356 | 0.156 | 0.541 |
| -2 | 0 | BLOSUM62 | 0.318 | 0.135 | 0.401 | 0.358 | 0.159 | 0.577 |
| -3 | 0 | BLOSUM62 | 0.318 | 0.135 | 0.401 | 0.350 | 0.156 | 0.535 |

FIG._6J-5

Query
Frame  MatID  Length  Eff.Length  E    S   W   T   X   E2    S2
+3     0      1889    1886        10.  35  3   12  22  0.15  35
+2     0      1890    1887        10.  35  3   12  22  0.15  35
+1     0      1890    1887        10.  35  3   12  22  0.15  35
-1     0      1890    1887        10.  35  3   12  22  0.15  35
-2     0      1890    1888        10.  35  3   12  22  0.15  35
-3     0      1889    1886        10.  35  3   12  22  0.15  35

Statistics:
Query          Expected    Observed                    HSPs        HSPs
Frame  MatID   High Score  High Score                  Reportable  Reported
+3     0       39 (17.9 bits)  141 (64.6 bits)         5           5
+2     0       39 (17.9 bits)   63 (28.9 bits)         4           4
+1     0       39 (17.9 bits)   37 (17.0 bits)         2           2
-1     0       39 (17.9 bits)   32 (14.7 bits)         0           0
-2     0       39 (17.9 bits)   43 (19.7 bits)         1           1
-3     0       39 (17.9 bits)   37 (17.0 bits)         0           0

Query          Neighborhd  Word   Excluded  Failed       Successful
Frame  MatID   Words       Hits   Hits      Extensions   Extensions
+3     0       25791       1930   372       1552         6
+2     0       30013       1929   366       1559         4
+1     0       28838       1602   316       1283         3
-1     0       22628       1714   279       1435         0
-2     0       24944       1732   270       1461         1
-3     0       25787       1767   320       1446         1

Database: /tmp/baaaaebva
  Release date: unknown
  Posted date: 4:08 PM PST Jan 31, 1997
# of letters in database: 1042
# of sequences in database: 1
# of database sequences satisfying E: 1
No. of states in DFA: 600 (118 KB)
Total size of DFA: 2679 KB (2687 KB)
Time to generate neighborhood: 0.21u  0.06s  0.03t  Real: 00:00:00
No. of processors used: 1
Time to search database: 0.03u  0.00s  0.03t  Real: 00:00:00
Total cpu time: 0.30u  0.06s  0.36t  Real: 00:00:00

Sequence Information Results

Library: STREPPY1

Orf ID(s): SP001074

| Asm Sequence ID | Contig Start | Contig End |
|---|---|---|
| 800003774F1 | 1035 | 1674 |
| 800012920F1 | 1054 | 1552 |
| 800009647F1 | 1071 | 1680 |
| 800013662F1 | 1320 | 1788 |
| 800005790F1 | 1414 | 2184 |
| 800013886F1 | 1534 | 2106 |
| 800001193F1 | 1797 | 2452 |
| 800003388F1 | 1891 | 2564 |
| 800003079F1 | 1900 | 2370 |
| 800003546F1 | 2014 | 2648 |
| 800010659F1 | 2084 | 2710 |
| 800016926F1 | 2115 | 2439 |
| 800005260F1 | 2153 | 2852 |
| 800006923F1 | 2168 | 2843 |

Sequence Information Results returned a total of 14 row(s).

[Main Menu] [Comparisons] [Gene List] [Org Info] [Sequences] [Southerns] [Help]

[Assembly] [Retrieve All]

FIG._6K

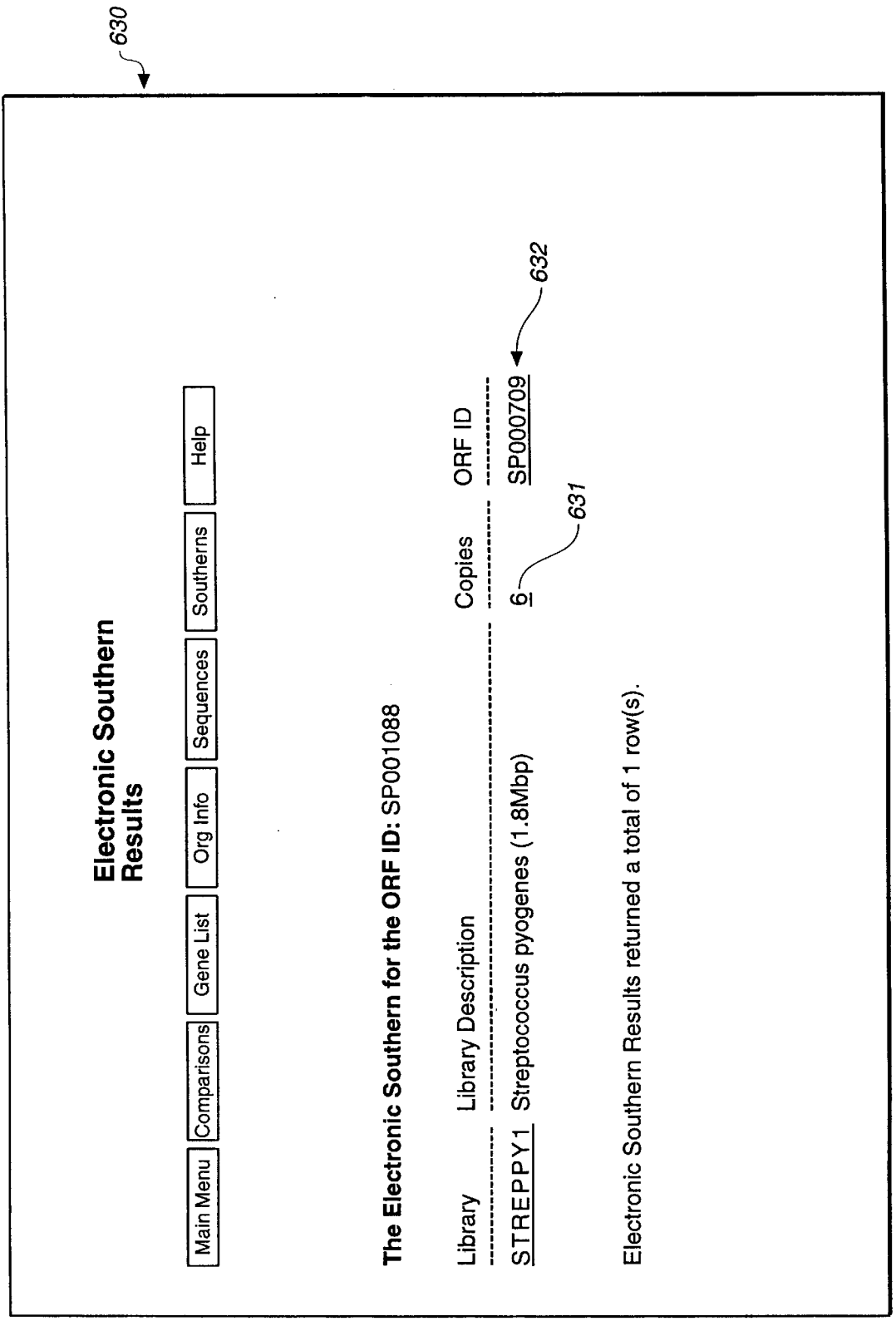
FIG._6L

Organism Gene Copies

| Main Menu | Comparisons | Gene List | Org Info | Sequences | Southerns | Help |

Library: STREPPY1

| Orf ID | Hit ID | Hit Description | DataSource | P-Value |
|---|---|---|---|---|
| SP0010188 | g881507 | hyaluronidase | gb97bctp | 0 |
| SP001327 | g881507 | hyaluronidase | gb97bctp | 0 |
| SP001278 | g881507 | hyaluronidase | gb97bctp | 1.2e-130 |
| SP0008885 | g881507 | hyaluronidase | gb97bctp | 3.1e-120 |
| SP001043 | g881507 | hyaluronidase | gb97bctp | 7.3e-26 |
| SP000709 | g881507 | hyaluronidase | gb97bctp | 7.8e-20 |

Organism Gene Copies returned a total of 6 row(s).

*FIG._6M*

Gene Locus Information

| Main Menu | Comparisons | Gene List | Org Info | Sequences | Southerns | Help |

Library: STREPPY1
Hit ID: g881507          Hit description: hyaluronidase

Contig ID: SPc00591     Length: 6333     Total Seqs: 47

| Orf ID | Hit ID | Hit Description | Hit DataSource | P-Value |
|---|---|---|---|---|
| SP001043 LUR | g881507 | hyaluronidase | gb97bctp | 7.3e-26 / 1 |
| SP001045 LUR | g153975 | flgJ flagellar protein | gb97bctp | 3.5e-10 / 1 |
| SP001047 LUR | g551669 | ORF | gb97bctp | 8.6e-11 / 1 |

Gene Locus Information Results returned a total of 6 row(s).

FIG._6N

Gene Locus Information

[ Main Menu ] [ Comparisons ] [ Gene List ] [ Org Info ] [ Sequences ] [ Southerns ] [ Help ]

Library: STREPPY1
Hit ID: g881507      Hit description: hyaluronidase

Contig ID: SPc00495      Length: 2699      Total Seqs: 23

| Orf ID | Hit ID | Hit Description | Hit DataSource | P-Value |
|---|---|---|---|---|
| | | | | 1 |
| LUR SP000709 | g881507 | hyaluronidase | gb97bctp | 7.8e-20 |

Gene Locus Information Results returned a total of 2 row(s).

Gene Locus Information

| Main Menu | Comparisons | Gene List | Org Info | Sequences | Southerns | Help |

Library: STREPPY1
Hit ID: g881507          Hit description: hyaluronidase

Contig ID: SPc00600    Length: 3805    Total Seqs: 51

| Orf ID | Hit ID | Hit Description | Hit DataSource | P-Value |
|---|---|---|---|---|
| LUR | | | | 1 |
| SP001088 | g881507 | hyaluronidase | gb97bctp | 0 |
| LUR | | | | 1 |

Gene Locus Information Results returned a total of 3 row(s).

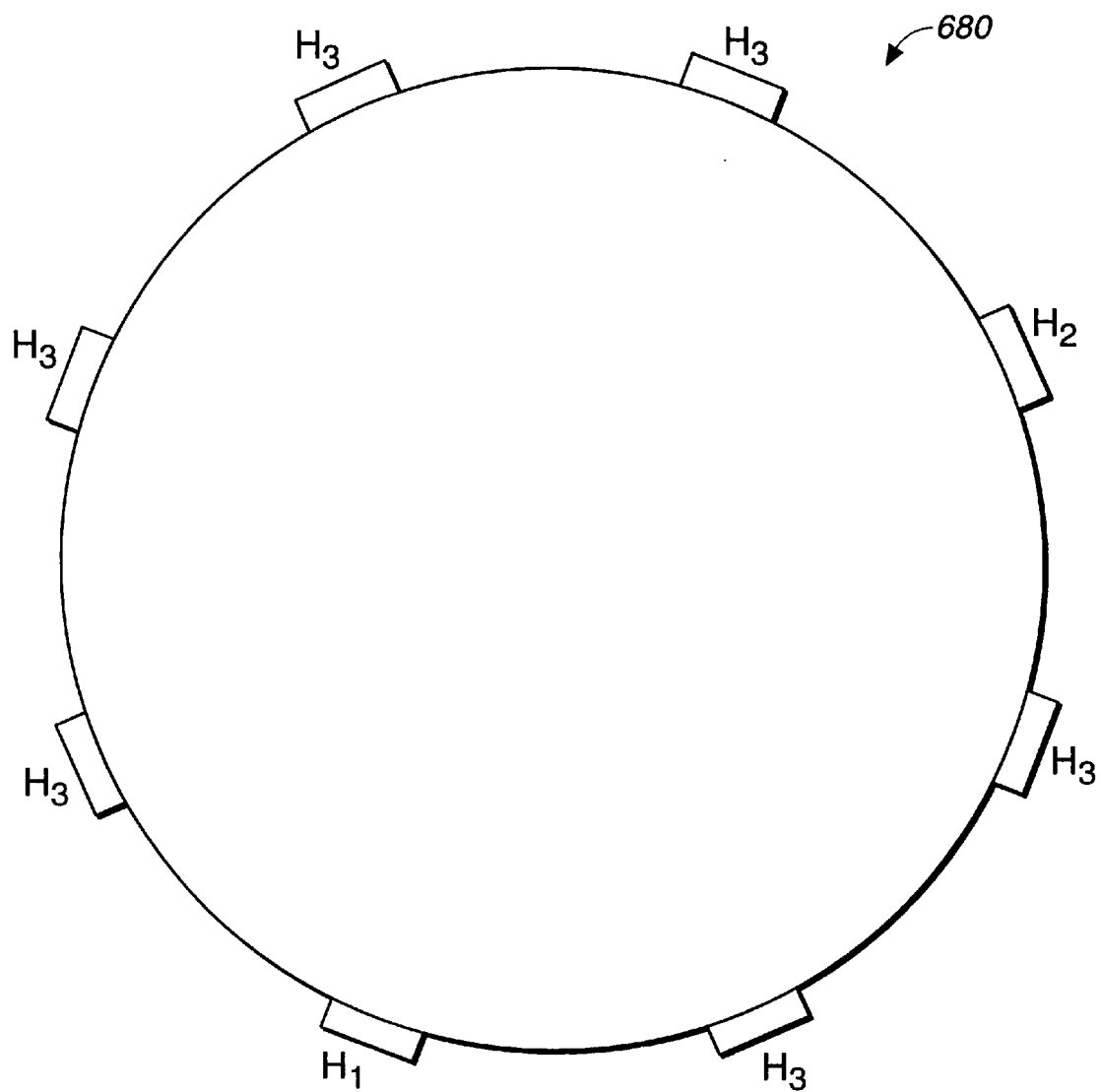
FIG._6Q

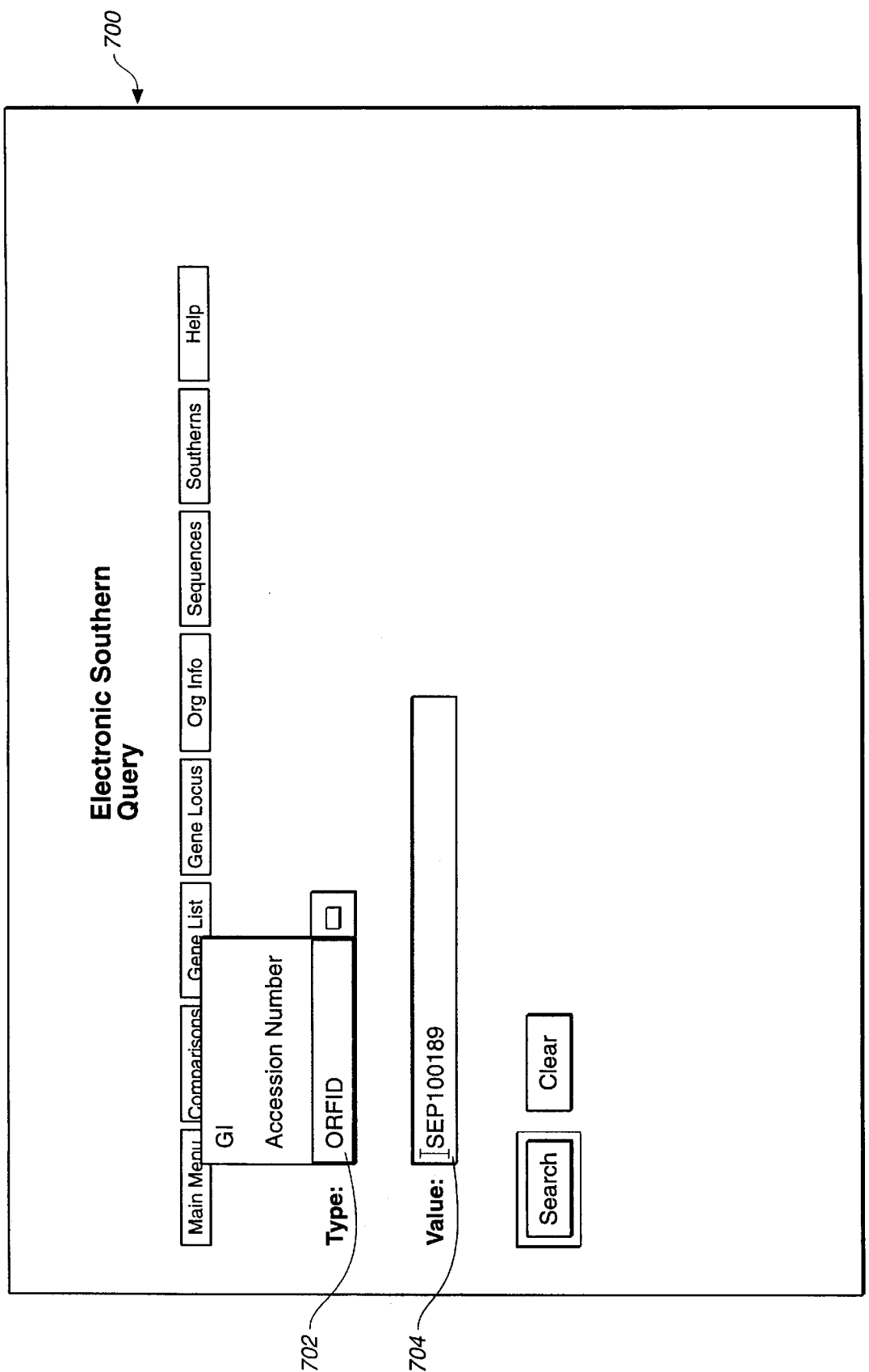
FIG._7A

Electronic Southern Results

| Main Menu | Comparisons | Gene List | Gene Locus | Org Info | Sequences | Southerns | Help |

| Multi-Align |

The Electronic Southern for the ORF ID: SEP100189  HitID: g755153  HitDescription: ATP-binding protein

| Library | Library Description | Copies |
|---|---|---|
| EFAECA01 | Enterococcus faecalis (2.8Mbp) | 2 |
| SAUREU01 | Staphylococcus aureus (2.8Mbp) | 1 |
| SEPIDE01 | Staphylococcus epidermidis (2.4Mbp) | 1 |
| SPYOGE01 | Streptococcus pyogenes (2.0Mbp) | 1 |
| SPYOGE02 | Streptococcus pyogenes (2.0Mbp) | 1 |
| SYNECH01 | Synechocystis sp. (3.6Mbp) | 3 |

Electronic Southern Results returned a total of 6 row(s).

*FIG._7B*

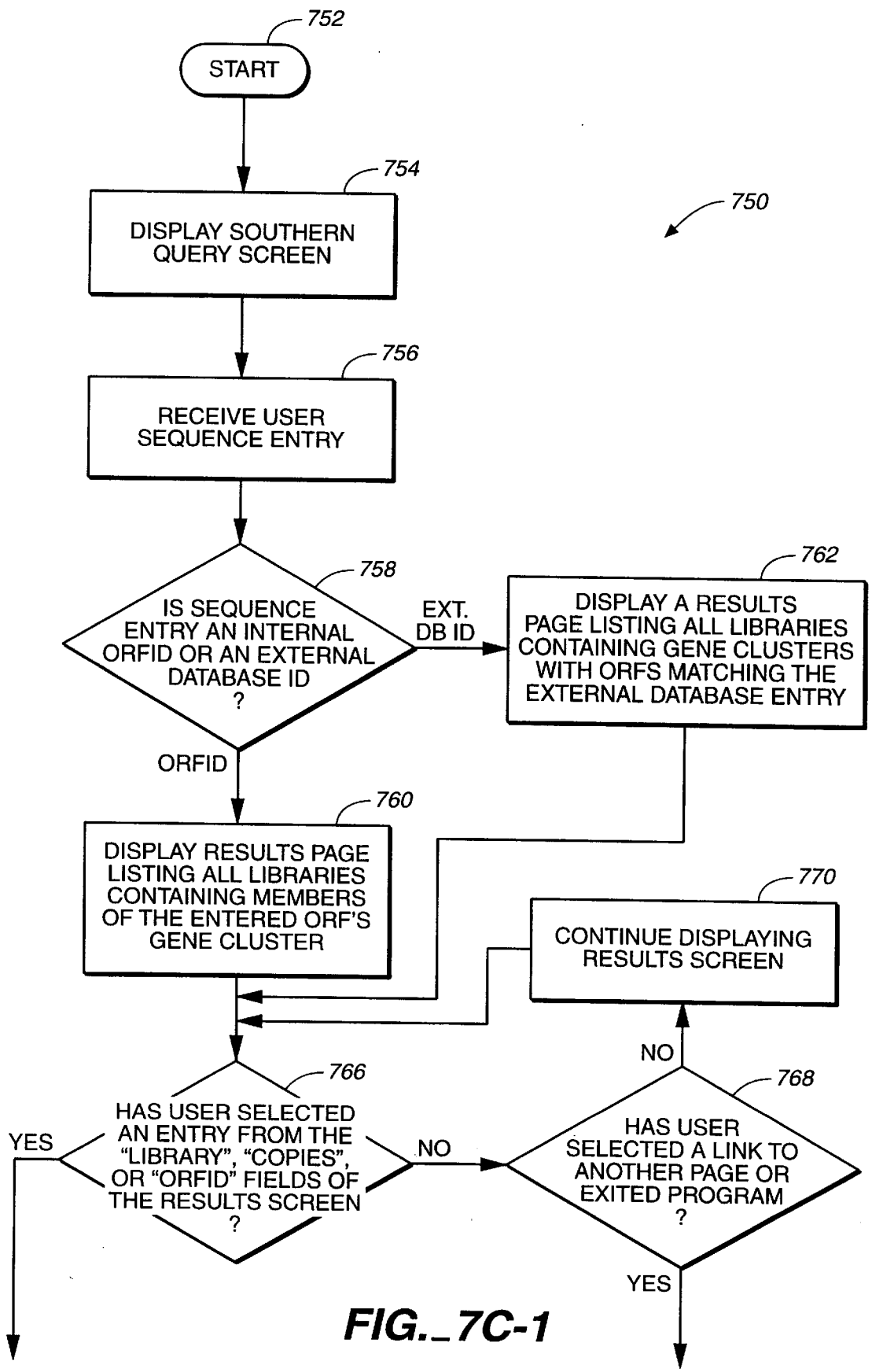
FIG._7C-1

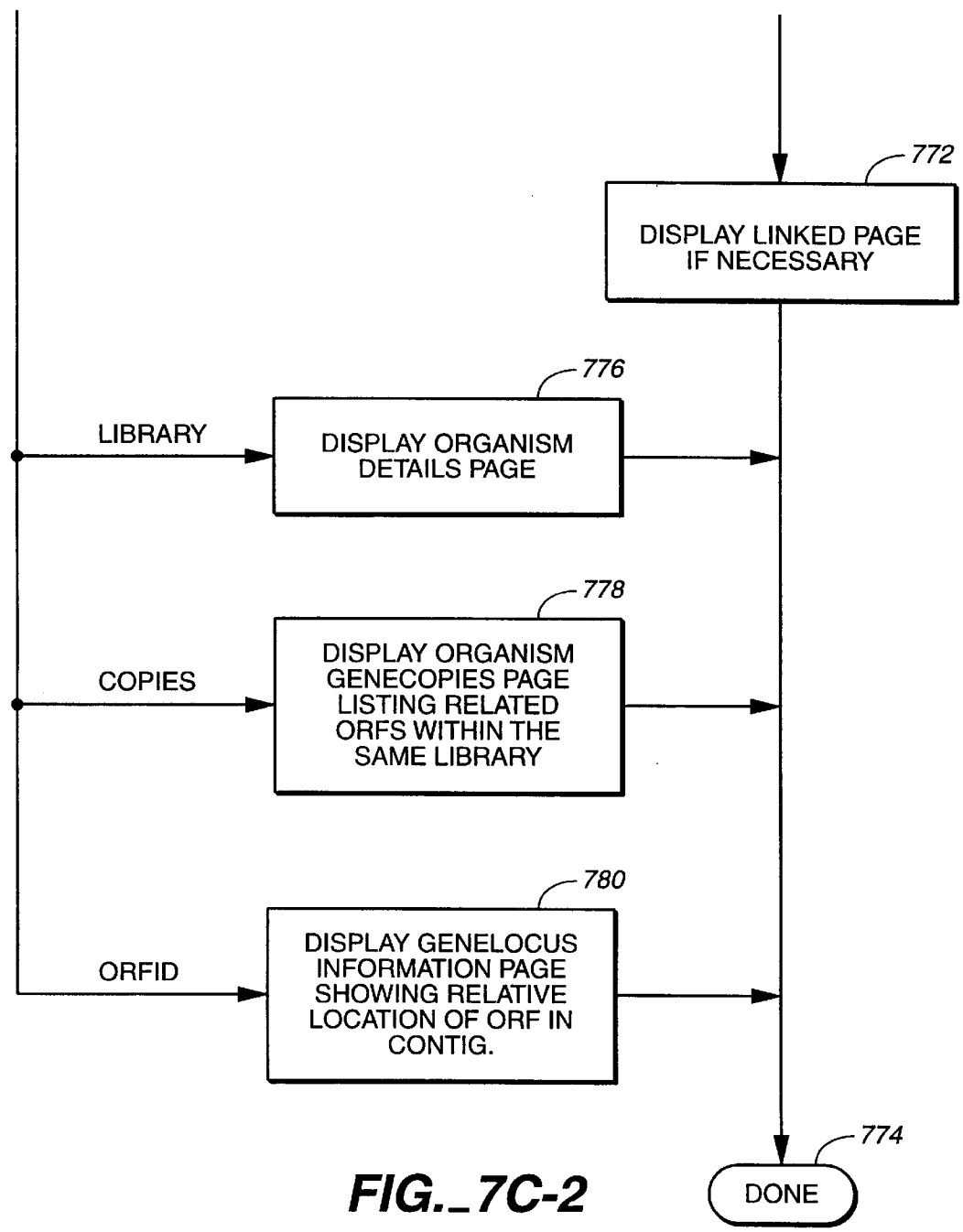

DATABASE AND SYSTEM FOR STORING, COMPARING AND DISPLAYING GENOMIC INFORMATION

CROSS REFERENCE TO RELATED APPLICATIONS

This application claims priority under 35 USC § 119(e) from U.S. Provisional patent application Ser. No. 60/032,565 (attorney docket no. ICYTP003+), filed Dec. 12, 1996 and entitled DATABASE OF MICROBIAL NUCLEIC ACID SEQUENCES. In addition, this application incorporates by reference in its entirety and for all purposes application Ser. No. 08/856,647 (attorney docket no. ICYTP003) entitled DATABASE AND SYSTEM FOR DETERMINING, STORING AND DISPLAYING GENE LOCUS INFORMATION, filed concurrently herewith.

BACKGROUND OF THE INVENTION

The present invention relates generally to relational databases for storing and retrieving biological information. More particularly the invention relates to systems and methods for providing sequences of biological molecules in a relational format allowing retrieval in a client-server environment.

Informatics is the study and application of computer and statistical techniques to the management of information. In genome projects, bioinformatics includes the development of methods to search databases quickly, to analyze nucleic acid sequence information, and to predict protein sequence, structure and function from DNA sequence data.

Increasingly, molecular biology is shifting from the laboratory bench to the computer desktop. Today's researchers require advanced quantitative analyses, database comparisons, and computational algorithms to explore the relationships between sequence and phenotype. Thus, by all accounts, researchers can not and will not be able to avoid using computer resources to explore gene sequencing, gene expression, and molecular structure.

One use of bioinformatics involves studying an organism's genome to determine the sequence and placement of its genes and their relationship to other sequences and genes within the genome or to genes in other organisms. Such information is of significant interest in biomedical and pharmaceutical research, for instance to assist in the evaluation of drug efficacy and resistance. To make genomic information manipulation easy to perform and understand, sophisticated computer database systems have been developed. In one database system, developed by Incyte Pharmaceuticals, Inc. of Palo Alto, Calif., genomic sequence data is electronically recorded and annotated with information available from public sequence databases. Examples of such databases include GenBank (NCBI) and TIGR. The resulting information is stored in a relational database that may be employed to determine relationships between sequences and genes within and among genomes.

Genetic information for a number of organisms has been catalogued in computer databases. Genetic databases for organisms such as *Eschericia coli, Haemophilus influenzae, Mycoplasma genitalium*, and *Mycoplasma pneumoniae*, among others, are publicly available. At present, however, complete sequence data is available for relatively few species, and the ability to manipulate sequence data within and between species and databases is limited.

While genetic data processing and relational database systems such as those developed by Incyte Pharmaceuticals, Inc. provide great power and flexibility in analyzing genetic information, this area of technology is still in its infancy and further improvements in genetic data processing and relational database systems will help accelerate biological research for numerous applications.

SUMMARY OF THE INVENTION

The present invention provides relational database systems for storing and analyzing biomolecular sequence information together with biological annotations detailing the source and interpretation of the sequence data. The present invention provides a powerful database tool for drug development and other research and development purposes.

Comparative Genomics is a feature of the database system of the present invention which allows a user to compare the sequence data of sets of different organism types. Comparative searches may be formulated in a number of ways using the Comparative Genomics feature. For example, genes common to a set of organisms may be identified through a "commonality" query, and genes unique to one of a set of organisms may be identified through a "subtraction" query.

Electronic Southern is a feature of the present database system which is useful for identifying genomic libraries in which a given gene or ORF exists. A Southern analysis is a conventional molecular biology technique in which a nucleic acid of known sequence is used to identify matching (complementary) sequences in a sample of nucleic acid to be analyzed. Like their laboratory counterparts, Electronic Southerns according to the present invention may be used to locate homologous matches between a "probe" DNA sequence and a large number of DNA sequences in one or more libraries.

The present invention provides a method of comparing genetic complements of different types of organisms. The method involves providing a database having sequence libraries with multiple biomolecular sequences for different types of organisms, where at least some of the sequences represent open reading frames located along one or more contiguous sequences on each of the organisms' genomes. The method further involves receiving a selection of two or more of the sequence libraries for comparison, determining open reading frames common or unique to the selected sequence libraries, and displaying the results of the determination.

The invention also provides a method of comparing genomic complements of different types of organisms. The method involves providing a database having genomic sequence libraries with multiple biomolecular sequences for different types of organisms, where at least some of the sequences represent open reading frames located along one or more contiguous sequences on each of the organisms' genomes. The method further involves receiving a selection of two or more of the sequence libraries for comparison, determining sequences common or unique to the selected sequence libraries, and displaying the results of the determination.

The invention further provides a computer system including a database containing genomic libraries for different types of organisms, which libraries have multiple genomic sequences, at least some of which representing open reading frames located along one or more contiguous sequences on each the organisms' genomes. The system also includes a user interface capable of receiving a selection of two or more genomic libraries for comparison and displaying the results of the comparison.

Another aspect of the present invention provides a method of identifying libraries in which a given gene exists. The method involves providing a database including genomic libraries for one or more types of organisms. The libraries have multiple genomic sequences, at least some of which represent open reading frames located along one or more contiguous sequences on each the organisms' genomes. The method further involves receiving a selection of one or more probe sequences, determining homologous matches between the selected probe sequences and the sequences in the genomic libraries, and displaying the results of the determination.

The invention also provides a computer system including a database including genomic libraries for one or more types of organisms, which libraries have multiple genomic sequences, at least some of which represent open reading frames located along one or more contiguous sequences on each the organisms' genomes. The system also includes a user interface capable of receiving a selection of one or more probe sequences for use in determining homologous matches between one or more probe sequences and the sequences in the genomic libraries, and displaying the results of the determination.

Also provided is a computer program product including a computer-usable medium having computer-readable program code embodied thereon relating to a database including genomic libraries for one or more types of organisms. The libraries have multiple genomic sequences, at least some of which represent open reading frames located along one or more contiguous sequences on each the organisms' genomes. The computer program product includes computer-readable program code for providing, within a computing system, an interface for receiving a selection of two or more genomic libraries for comparison, determining sequences common or unique to the selected genomic libraries, and displaying the results of the determination.

Additionally provided is a computer program product including a computer-usable medium having computer-readable program code embodied thereon relating to a database including genomic libraries for one or more types of organisms. The libraries have multiple genomic sequences, at least some of which represent open reading frames located along one or more contiguous sequences on each the organisms' genomes. The computer program product includes computer-readable program code for providing, within a computing system, an interface for receiving a selection of one or more probe open reading frames, determining homologous matches between the probe sequences and the sequences in the genomic libraries, and displaying the results of the determination.

The invention further provides a method of presenting the genetic complement of an organism. The method involves providing a database including sequence libraries for a plurality of types of organisms, where the libraries have multiple biomolecular sequences, at least some of which represent open reading frames located along one or more contiguous sequences on each of the organisms' genomes. The methof further involves receiving a selection of one of the sequence libraries, determining open reading frames within the selected sequence library, and displaying the results as one or more unique identifiers for groups of related opening reading frames.

These and other features and advantages of the invention will be described in more detail below with reference to the drawings.

BRIEF DESCRIPTION OF THE DRAWINGS

FIG. 1 is a flow diagram presenting key steps employed to generate data for a database in accordance with one embodiment of the present invention.

FIG. 2A is a block diagram of a client-server Intranet for providing database services in accordance with one embodiment of the present invention.

FIG. 2B is a schematic representation of the various software documents and entities employed by the FIG. 2A client-server Intranet to provide biological information in response to user queries.

FIG. 3 is a physical data model for a genomic relational database in accordance with a preferred embodiment of the present invention.

FIG. 4 is a logical data model for a genomic relational database in accordance with a preferred embodiment of the present invention.

FIG. 5A is a screen (HTML page) display presenting a Main Menu for a graphical user interface of a genomic sequences database in accordance with one embodiment of the present invention.

FIG. 5B is an Organism Information Results screen for a graphical user interface in accordance with a preferred embodiment of the present invention, allowing users to view a list of each organism library available in the database of the present invention.

FIG. 5C is a Gene List Query screen for a graphical user interface in accordance with a preferred embodiment of the present invention, allowing users to enter a search query to display ORFs from a selected library.

FIG. 5D is a Gene List Results screen for a graphical user interface in accordance with a preferred embodiment of the present invention, displaying ORFs from a library selected in the query screen depicted in FIG. 5C.

FIG. 5E is a Gene Locus Query screen for a graphical user interface in accordance with a preferred embodiment of the present invention, allowing users to enter a search query to display the genomic position of ORFs from a selected library.

FIG. 5F is a Gene Locus Results screen for a graphical user interface in accordance with a preferred embodiment of the present invention, displaying the positions of ORFs in response to a search query entered in the query screen depicted in FIG. 5E.

FIGS. 6A is a screen shot of a user interface screen provided for accepting user queries pertaining to a Comparative Genomics search according to a preferred embodiment of the present invention.

FIG. 6B is a screen shot of a user interface screen provided for displaying the results of a Comparative Genomics search according to a preferred embodiment of the present invention.

FIG. 6C is a flow chart depicting the process flow by which a user can conduct a comparative genomic analysis within a graphical user interface in accordance with a preferred embodiment of the present invention.

FIG. 6D is a Venn diagram illustrating the results of a Comparative Genomics subtraction query according to one embodiment of the present invention.

FIGS. 6E–6P are user interface screen shots which illustrate an example of a Comparative Genomics subtraction query according to one embodiment of the present invention.

FIG. 6Q depicts a hypothetical microbial genome having eight open reading frames from three different gene clusters all of which relate to genes having common functionality identified in the preceding example.

FIG. 7A is a screen shot of a user interface screen provided for accepting user queries pertaining an Electronic Southern analysis.

FIG. 7B is a screen shot of a user interface screen provided to display results of a user's Electronic Southern query.

FIG. 7C is a process flow diagram a user interface process by which a user can conduct an Electronic Southern analysis within a graphical user interface in accordance with a preferred embodiment of the present invention.

DETAILED DESCRIPTION OF THE PREFERRED EMBODIMENTS

Figures 1, 6F:
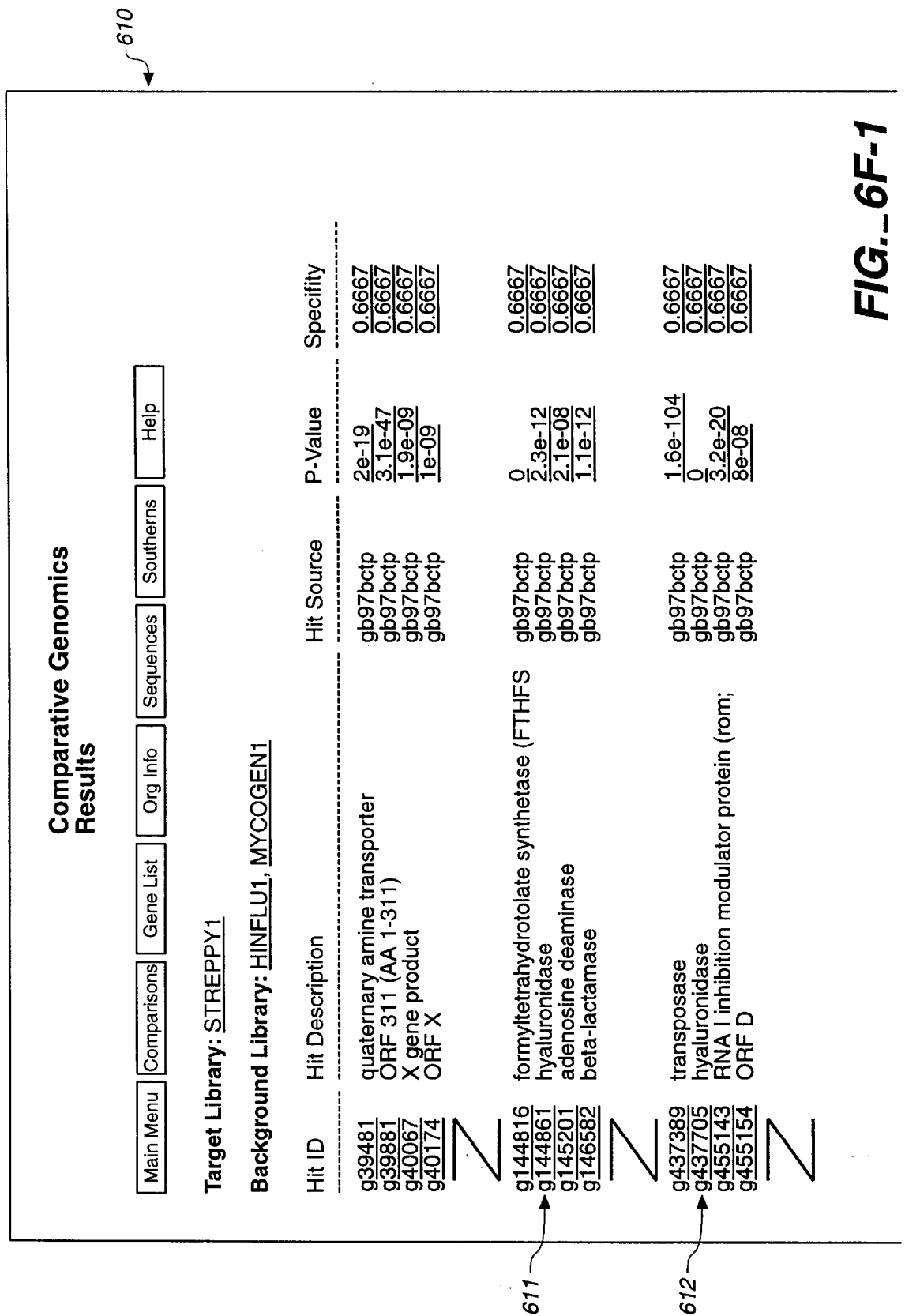

Generally, the present invention provides an improved relational database for storing and manipulating genomic sequence information. While the invention is described in terms of a database optimized for microbial data, it is by no means so limited. For example, the invention covers databases optimized for other sources of sequence data, such as animal sequences (e.g., human, primate, rodent, amphibian, insect, etc.) and plant sequences. In the following description, numerous specific details are set forth in order to provide a thorough understanding of the present invention. It will be apparent, however, that the present invention may be practiced without limitation to some of the specific details presented herein.

1. Introduction and Relevant Terminology

The following terms are used throughout the specification. The descriptions are provided to assist in understanding the specification, but do not necessarily limit the scope of the invention.

Internal database—This is the focus database of this invention. It contains biomolecular sequences and may also contain information associated with sequences such as libraries in which a given sequence is found or not found, descriptive information about a likely gene associated with the sequence, the position of the sequence in its organism's genome, etc. The database may be divided into two parts: one for storing the sequences themselves and the other for storing the associated information. This database may sometimes be referred to as a "local" or "enterprise" database.

The internal database may typically be maintained as a private database behind a firewall within an enterprise. However, this invention is not so limited and the internal database could actually be made available to the public. Examples of private internal databases include the LifeSeq™ and PathoSeq™ databases available from Incyte Pharmaceuticals, Inc. of Palo Alto, Calif.

Sequence database—When the internal database is designed to include separate parts, one of these may be a sequence database which contains sequences of biomolecules in an internal database.

Genomic database—When the internal database is designed to include separate parts, one of these may be a genomic database containing genomic information about the sequences in the sequence database. As noted, such information may include genomic libraries in which a given sequence is found or not found, descriptive information about a likely gene associated with the sequence, the position of the sequence in its organism's genome.

External database—This is a database located outside the internal database. Typically, it will be maintained by an enterprise that is different from the enterprise maintaining the internal database. In the context of this invention, the external database is used primarily to obtain information about the various sequences stored in the internal database. The external database may be used, for example, to provide some descriptive information stored in the genomics database. Examples of such external databases include the GenBank database maintained by the National Center for Biotechnology Information (NCBI), part of the National Library of Medicine, and the TIGR database maintained by The Institute for Genomic Research.

Record—This term generally refers to a row in a database table. Each record contains one or more fields or attributes. A given record may be uniquely specified by one or a combination of fields or attributes known as the record's primary key.

ORF—an Open Reading Frame; corresponds to a nucleotide sequence which could potentially be translated into a polypeptide. Such a stretch of sequence is uninterrupted by a stop codon. An ORF that represents the coding sequence for a full protein begins with an ATG "start" codon and terminates with one of the three "stop" codons. For the purposes of this application, an ORF may be any part of a coding sequence, with or without start and/or stop codons. For an ORF to be considered as a good candidate for coding for a bona fide cellular protein, a minimum size requirement is often set, for example, a stretch of DNA that would code for a protein of 50 amino acids or more. An ORF is not usually considered an equivalent to a gene or locus until there has been shown to be a phenotype associated with a mutation in the ORF, an mRNA transcript for a gene product generated from the ORF's DNA has been detected, and/or the ORF's protein product has been identified.

Library—Physically, a pool of DNA fragments that is propagated in a cloning vector. As used more frequently in the present application, library refers to an electronic collection of genomic sequence data, including raw sequences, contigs, ORFs and loci from a specific organism.

Cluster—This is a group of ORFs related to one another by sequence homology. Clusters are generally formed based upon a specified degree of homology and overlap (e.g., a stringency).

Annotation—A functional description of an ORF, which may include identifying attributes such as locus name, key words, and Medline references.

BLAST—The Basic Local Alignment Search Tool; a technique for detecting ungapped sub-sequences that match a given query sequence. BLAST is used in one embodiment of the present invention as a preliminary step in detecting ORF boundaries in the Gene Finding module.

BLASTP—A BLAST program that compares an amino acid query sequence against a protein sequence database.

BLASTX—A BLAST program that compares the six-frame conceptual translation products of a nucleotide query sequence (both strands) against a protein sequence database. In one embodiment of the present invention, it is used to create a sub-database of ORFs which may exist on a contig, and to identify the best match between one of these ORFs and a sequence in an external database.

FASTA—A modular set of sequence comparison programs used to compare an amino acid or DNA sequence against all entries in a sequence database. FASTA was written by Professor William Pearson of the University of Virginia Department of Biochemistry. The program uses the rapid sequence algorithm described by Lipman and Pearson (1988) and the Smith-Waterman sequence alignment protocol. FASTA performs a protein to protein comparison in the annotation of ORFs defined during Gene Finding.

FASTX—A module of the FASTA protocol used to define optimal ORF boundaries during Gene Finding. FASTX uses a nucleotide to protein sequence comparison.

cds—In a GenBank DNA sequence entry, "cds" stands for coding sequence. A coding sequence is a sub-sequence of a DNA sequence that is surmised to encode a gene. A complete gene coding sequence begins with an "ATG" and ends with a stop codon.

Contig—A group of assembled overlapping sequences.

Paralogs or Copies—The number of related ORFs within a library.

GenPept—A public bacterial peptide database; part of the GenBank family of databases.

Hit Threshold—A pre-set E-value or P-value for evaluating sequence matches. In a preferred embodiment, this value is generally set at 1e-6 for Gene Finding; and at 1e-15 for Gene Clustering.

Orphan Contig—A contig without identified ORFs.

P-value—A result of BLAST searches; this number indicates the probability that a match between two sequences is due to random chance.

E-value—A result of a FASTA analysis; this number indicates the probability that a match between two sequences is due to random chance.

Southern—As most frequently used herein, an electronic analog of the laboratory technique known as Southern blotting, this analysis identifies libraries in which a given gene or ORF is present.

NumLibs—The number of libraries in which a given gene or ORF is present.

Coverage—The percentage of the genome that is covered by the contigs in an enterprise database.

Depth—provides information relating to the depth of coverage of an enterprise sequenced genome. The value of this attribute is dierectly related the amount of sequencing done for an organism's genome, and typically reflects the average depth of coverage.

2. Genome Sequencing, Data Processing and Populating the Genomic Relational Database The following description presents one preferred process by which data for a source database according to the present invention may be obtained. While the embodiment described below relates to microbial genomic data, the invention is also applicable to genomic data from other sources. The process is illustrated in FIG. 1.

In one embodiment, the database of the present invention may contain genomic data from a number of sources, including data from external sources, such as public databases. In addition, enterprise genomic data, that is, proprietary data obtained and processed by the database developer, is generally used.

a. Library Construction/Genome Sequencing

Enterprise-derived genomic data may be obtained by various DNA isolation and sequencing procedures known to those of skill in the art. In one example of such a procedure, genomic DNA from a particular microbial organism is isolated and then mechanically sheared, blunt-ended, gel-purified, and cloned into suitable vectors, for instance, pBluescript SK vectors. Typically, enough DNA is sequenced to provide three to five times depth of coverage of the organism's genome. The vectors are then transformed into *E. coli* bacterial cells and grown overnight. Thereafter, colonies, each representing a clone of a particular fragment of the organisms genome, may be picked from this library, and a colony's plasmid DNA may be isolated for sequencing. In the process flow of FIG. 1A, the process begins at 102, and the above-described library construction operations are represented by step 104.

As represented by step 105, sequencing templates for a clone's DNA are then prepared and sequencing reads are performed, for example, on an Applied Biosystems, Inc. (ABI) Prism 377 DNA Sequencer, which includes a "base caller" program. Average read lengths are generally greater than about 500 bases. In a preferred embodiment, a second base caller, Phred, may then be used to attribute quality scores to each of the bases. In this way, each base in the sequence will have an associated confidence level. Each genomic sequence fragment is then specifically identified with a Sequence ID.

b. Data Processing

Enterprise-derived sequences and external sequences are processed through an automated "bioanalysis" system before incorporation into the database of the present invention. External sequences, which may be obtained, for instance, through NCBI, are also typically partially processed, as further discussed below. In a preferred embodiment, the bioanalysis system is composed of a linked series of proprietary and public software tools, which automatically analyze each genomic sequence and deposit it into the database. In a preferred embodiment, the system may include four (4) independent modules designated: Sequence Editing, Contig Formation, Gene Finding, and Gene-Clustering.

(i) Sequence Editing

The sequence editing module, represented by step 106 in process flow 100, aims to remove extraneous sequence data ("contaminants"), such as vector sequences, from the microbial genome sequence fragments. During this process, the first 30 bases from the 5' end of each sequence fragment, which generally contain extraneous information, are removed from the sequence. Vector recognition and removal is then performed on both the 5' and 3' ends of each sequence fragment. Each resulting sequence is then compared to various known contaminants. If the sequences are contaminated, they are removed from the library.

(ii) Contig Formation

As represented by step 108 in process flow 100, the edited sequences are then assembled into "contigs" in the second module. As previously noted, contigs are consensus groupings of at least partially overlapping sequences. In a preferred embodiment, contig formation may be accomplished using Phrap (phragment assembly program), a sequence assembly algorithm developed at the University of Washington. This program takes a file of raw ("shotgun") DNA sequence fragments and attempts to align them. Alignments are influenced by the quality scores which have been assigned to the individual bases of the sequence fragments during the sequencing/base calling processes. The result of this process is the assembly of a number of overlapping contiguous DNA sequences (contigs) from the organism's genome.

A typical microbial genome may be represented by hundreds of contigs, depending upon the depth of coverage in sequencing. Following the assembly process, each contig is specifically identified with a ContigID. Single sequences that do not align with other sequences may be designated as individual contigs. A sequence cannot belong to more than one contig. Contigs and the underlying sequences from which they are derived may be uniquely identified by their assigned IDs. Each ContigID may contain one or more associated SequenceIDs. Generally, external genome sequences are not run through the assembly program because they are usually submitted as a single contiguous sequence, rather than being provided as raw sequence data. Accordingly, these external genome sequences are generally assigned a single ContigID without associated SequenceIDs.

In summary, ContigID refers to a consensus sequence derived from assembled sequences, while SequenceID refers to a particular sequence derived from a microbial genomic clone. SequenceIDs will remain constant throughout subsequent data processing and manipulation. ContigIDs, however, may change, particularly as new sequences are obtained which may bridge multiple contigs into one. In a preferred embodiment, a further identifier, NumSeqs may be used to indicate the number of sequences assembled to form an unannotated contig or open reading frame (see below).

(iii) Gene Finding

Next, as represented by step 110 in process flow 100, Gene Finding attempts to identify "ORF"s located on the contigs formed in the previous module. As noted previously, an ORF is an open reading frame, which corresponds to a stretch of DNA that could potentially be translated into a polypeptide. In a preferred embodiment, ORF identification is carried out using a series of searches for similarity matches ("hits"), which may include overlap regions of identical base pairs or close homology, between the consensus sequences of the contigs assembled in the previous module against already-identified sequences in public-domain databases or other external sources. These hits indicate the ORFs within the genome.

The ORF identification process attempts to indirectly assign ORFs to a locus on a contig. If a match is found which satisfies one or more thresholds of probability of homology (referred to as a P-values (BLAST) or E-values (FAST), then the matching locus on the contig is annotated as an ORF. In this embodiment, both the E-Value and the P-value reflect the probability that a match between a database contig sequence or an external genome ORF sequence and a GenPept sequence is not due to random chance. Therefore, the lower the P-value and E-value, the greater the chance the sequences are related. A minimum threshold value (for both P-value and E-value) for a match in the Gene Finding module is generally set, for example, equal to or less than 1e-6.

To identify such hits, one or more sequence alignment algorithms such as BLAST (Basic Local Alignment Search Tool) or FAST (using the Smith-Waterman algorithm) may be employed. In a particularly preferred embodiment, these two alignment protocols are used in combination. Both of these algorithms look for regions of similarity between two sequences; the Smith-Waterman algorithm is generally more tolerant of gaps, and is used to provide a higher resolution match after the BLAST search provides a preliminary match. These algorithms determine (1) alignment between similar regions of the two sequences, and (2) a percent identity between sequences. For example, alignment may be calculated by matching, base-by-base, the regions of substantial similarity.

A particularly useful BLAST protocol for a preliminary Gene Finding step is BLASTX. The consensus nucleotide sequence of each contig is analyzed against a public database, such as the GenBank Peptide (GenPept) database. A BLASTX search compares the six-frame conceptual translation products of a nucleotide query sequence (contig) against a protein sequence database (GenPept). The result of this preliminary alignment is a subset of GenPept having homology to the contig against which further alignment searches may be run. In a preferred embodiment, a second BLASTX analysis is run against the previously determined GenPept subset in order to identify the best match ("top hit"), based on P-value, between the contig and a gene in the GenPept subset. A FASTX alignment is then performed between the original contig and the top hit. This analysis identifies the best alignment within the region of homology between the contig and the top hit identified by the BLAST searches. This sequence is then identified as an ORF, whether or not the analysis identifies the exact start and stop regions of the ORF.

The protein translation for the ORF is deposited in an ORF database (identified as "paorfp" in the embodiment described below), and the identified region on the original contig is masked (e.g., by Ns, which the program will subsequently ignore). The contig, now with the first identified ORF region masked, is run against GenPept again using BLAST and FAST to find the next top hit and alignment. This process continues until there are no more hits with a P-value less than 1e-6 to GenPept.

Contigs that have no more regions (or no regions at all) with ORF matches in the public database may contain previously uncharacterized ORFs. These ORFs, if present, are located with the use of an ORF finding program, such as GeneMark, which is an algorithm for identifying putative ORFs based on codon usage rather than homology to known genes. The GeneMark program is available from Georgia Tech University (through Georgia Tech Research Corporation). Putative ORFs identified in this manner are also deposited in the ORF database of the present invention.

After identifying the ORFs on a contig, a FASTA search is run between each ORF and GenPept to look for the best match to use for annotation purposes. The search is run using a translation of ORFs to their protein sequences and matching against annotated protein sequence databases in order to minimize inaccuracies associated with the degeneracy of the genetic code. When the best match is found at an E-value equal to or less than a threshold value, for example 1e-6, the ORF inherits the associated GenBank Identifier (GI) number and annotations from the GenPept sequence. Thia annotation feature is represented by step 112 in process flow 100.

In addition, as represented by step 111, a FASTA search is run against GenPept for each ORF already identified in the public genomes. This search is essentially a redundant process since the ORFs for a public genome have already been identified. However, if a different top match is found at an E-value equal to or less than the minimum threshold value (e.g., 1e-6), the ORF will be reannotated according to the new match.

Within those contigs for which there are ORF matches, there may also be unannotated regions that are 500 bases or longer. These regions are known as Long-Unannotated Regions (LURs), which may contain novel ORFs, transfer RNAs, or ribosomal RNAs. This 500 base value is based on comparative analysis of the lengths of ORFs and unannotated regions. If a contig has been run through the ORF identification process without finding any ORF matches, it is identified as an Orphan Contig.

In a preferred embodiment of the database of the present invention, GenPept matches are signified by the presence of a GI number (gxxxx). All sequences in GenBank databases are assigned an arbitrary GenBank identifier (GI) number, which serves as a unique tag for that sequence. This GI number may thereafter be used to identify the sequence and/or its associated contig in subsequent database analyses and manipulations.

After the ORFs on a contig have been identified, each ORF is assigned an ORFID number. ORFIDs are generally assigned sequentially for a single contig, beginning from sequence coordinate 0 at the 5' end and proceeding to the 3' end of the contig. Contigs are selected at random, and therefore, ORFIDs for an enterprise genome are not intended to indicate contig ordering or relationships in the actual genome.

ORFIDs for external genomes are assigned to a linear representation of the genome. The numbering begins with ORF 1 at sequence coordinate 0 and proceeds in a 3' direction. The database maintains the ORF ID assignment for these external genomes.

(iv) Gene Clustering

In the final module of bioanalysis, represented by step 114 in process flow 100, a Gene Clustering protocol is used to determine related ORFs within and across genomes. Gene Clustering for ORFs assigned to enterprise genomes uses the protein translation for an ORF and performs a pair-wise comparison against every ORF in its own library as well as every ORF in all other available libraries, using a FASTA protocol. ORFs that match each other at a threshold E-value, for example 1e-15, or smaller are grouped together in a cluster. The representative ORF within a cluster is the one with the best match to its annotating hit. Each Gene Cluster is assigned a unique Gene Cluster ID ("GeneCluID").

The FASTA pair-wise analysis also allows for transitive comparisons of organism libraries. That is, if an ORF from library A is clustered with an ORF in library B, and that ORF from library B clusters with an ORF in library C, the library A and C ORFs may be clustered together, even if a direct comparison of A and C would not have resulted in the two ORFs being clustered together. This functionality allows for the identification of more distant relationships between ORFs of different organisms. Pair-wise comparisons also provide optimal comparisons of genomes with vastly different sizes.

c. Database Population

Following completion of the Gene Clustering module, the data is loaded into the database, as represented by step 116 in process 100. In a preferred embodiment, the relational database includes a "sequence module" and a "genomic module". The sequence module stores unannotated sequences (provided as pure nucleic acid sequences, for example) determined for the isolated genomic DNA. The genomic module identifies the sequences by SequenceIDs (without necessarily providing raw sequences) and includes annotated information regarding each of the so identified sequences. In a preferred embodiment, the annotations may be roughly classified as either (1) information about how the sequences relate to one another, and (2) where the sequences originated. The process concludes at 118.

A number of computer platforms can be used to perform the necessary calculations for various algorithmic processes employed in the data processing process illustrated in flow 100 (e.g., assembling and clustering the sequences). For example, a number of computer workstations from a variety of manufacturers can be used. In particular, workstations produced by Silicon Graphics, Inc. (SGI) of Mountain View, Calif. and multiprocessor (e.g. 12 processor) Alpha™ systems manufactured by Digital Electronics Corporation (DEC) of Maynard, Mass. have been found to be suitable for performing such calculations.

3. The Database Environment

FIG. 2A depicts a network system 130 suitable for storing and retrieving information in relational databases of the present invention. Network 130 includes a network cable 134 to which a network server 136 and clients 138*a* and 138*b* (representative of possibly many more clients) are connected. Cable 134 is also connected to a firewall/gateway 140 which is in turn connected to the Internet 142.

Network 130 may be any one of a number of conventional network systems, including a local area network (LAN) or a wide area network (WAN), as is known in the art (e.g., using Ethernet, IBM Token Ring, or the like). The network includes functionality for packaging client calls in a well-known format (e.g., URL) together with any parameter information into a format (of one or more packets) suitable for transmission across a cable or wire 134, for delivery to database server 136.

Server 136 includes the hardware necessary for running software to (1) access database data for processing user requests, and (2) provide an interface for serving information to client machines 138*a* and 138*b*. In a preferred embodiment, depicted in FIG. 2A, the software running on the server machine supports the World Wide Web protocol for providing page data between a server and client.

Client/server environments, database servers, relational databases and networks are well documented in the technical, trade, and patent literature. For a discussion of database servers, relational databases and client/server environments generally, and SQL servers particularly, see, e.g., Nath, A., *The Guide To SQL Server*, 2nd ed., Addison-Wesley Publishing Co., 1995 (which is incorporated herein by reference for all purposes).

As shown, server 136 includes an operating system 150 (e.g., UNIX) on which runs a relational database management system 152, a World Wide Web application 154, and a World Wide Web server 156. The software on server 136 may assume numerous configurations. For example, it may be provided on a single machine or distributed over multiple machines.

World Wide Web application 154 includes the executable code necessary for generation of database language statements (e.g., Standard Query Language (SQL) statements). Generally, the executables will include embedded SQL statements. In addition, application 154 includes a configuration file 160 which contains pointers and addresses to the various software entities that comprise the server as well as the various external and internal databases which must be accessed to service user requests. Configuration file 160 also directs requests for server resources to the appropriate hardware—as may be necessary should the server be distributed over two or more separate computers.

Each of clients 138*a* and 138*b* includes a World Wide Web browser for providing a user interface to server 136. Through the Web browser, clients 138*a* and 138*b* construct search requests for retrieving data from a sequence database 144 and/or a genomic database 146. Thus, the user will typically point and click to user interface elements such as buttons, pull down menus, scroll bars, etc. conventionally employed in graphical user interfaces. The requests so formulated with the client's Web browser are transmitted to Web application 154 which formats them to produce a query that can be employed to extract the pertinent information from sequence database 144 or genomic database 146.

In the embodiment shown, the Web application accesses data in genomic database 146 by first constructing a query in a database language (e.g., Sybase or Oracle SQL). The database language query is then handed to relational database management system 152 which processes the query to extract the relevant information from database 146. In the case of a request to access sequence database 144, Web application 154 directly communicates the request to that database without employing the services of database management system 152.

The procedure by which user requests are serviced is further illustrated with reference to FIG. 2B. In this embodiment, the World Wide Web server component of server 136 provides Hypertext Mark-up Language documents ("HTML pages") 164 to a client machine. At the client machine, the HTML document provides a user interface 166 which is employed by a user to formulate his or her requests for access to database 146. That request is converted by the Web application component of server 136 to a SQL query 168. That query is used by the database management system component of server 136 to access the relevant data in database 146 and provide that data to server 136 in an appropriate format. Server 136 then generates a new HTML document relaying the database information to the client as a view in user interface 166.

While the embodiment shown in FIG. 2A employs a World Wide Web server and World Wide Web browser for a communication between server 136 and clients 138a and 138b, other communications protocols will also be suitable. For example, client calls may be packaged directly as SQL statements, without reliance on Web application 154 for a conversion to SQL.

When network 130 employs a World Wide Web server and clients, it must support a TCP/IP protocol. Local networks such as this are sometimes referred to as "Intranets." An advantage of such Intranets is that they allows easy communication with public domain databases residing on the World Wide Web (e.g., the GenBank World Wide Web site). Thus, in a particular preferred embodiment of the present invention, clients 138a and 138b can directly access data (via Hypertext links for example) residing on Internet databases using a HTML interface provided by Web browsers and Web server 156.

Bare in mind that if the contents of the local databases are to remain private, a firewall 140 must preserve in confidence the contents of a sequence database 144 and a genomics database 146.

In a preferred embodiment, sequence database 144 is a flat file database including separate partitions for genomic sequences from different species. Other possible approaches may include partitioning the sequence data according to whether or not sequences have been found to be unique to the local database (i.e., sequences that did not have any hits in an external database such as GenBank).

Preferably, the information in genomic database 146 is stored in a relational format. Such a relational database supports a set of operations defined by relational algebra. It generally includes tables composed of columns and rows for the data contained in the database. Each table has a primary key, being any column or set of columns the values of which uniquely identify the rows in the table. The tables of a relational database may also include a foreign key, which is a column or set of columns the values of which match the primary key values of another table. A relational database is also generally subject to a set of operations (select, project, product, join and divide) which form the basis of the relational algebra governing relations within the database. As noted above, relational databases are well known and documented (see, e.g., Nath, A., *The Guide To SQL Serve*, referenced above).

A relational database may be implemented in different ways. In Oracle™ databases, for example, the various tables are not physically separated, as there is one instance of work space with different ownership specified for different tables. In Sybase™ databases, in contrast, the tables may be physically segregated into different "databases."

One specific configuration for network 130 for multiple users provides both the genomics and sequence databases on the same machine. If there is a high volume of sequence searching, it may be desirable to have a second processor of similar size and split the application across the two machines to improve response time.

A suitable dual processor server machine may be any of the following workstations: Sun-Ultra-Sparc 2™ (Sun Microsystems, Inc. of Mountain View, Calif.), SGI-Challenge L™ (Silicon Graphics, Inc. of Mountain View, Calif.), and DEC-2100A™ (Digitial Electronics Corporation of Maynard, Mass.). Multiprocessor systems (minimum of 4 processors to start) may include the following: Sun-Ultra Sparc Enterprise 4000™, SGI-Challenge XL™, and DEC-8400™. Preferably, the server machine is configured for network 130 and supports TCP/IP protocol.

Depending upon the workstation employed, the operating system may be, for example, one of the following: Sun-Sun OS 5.5 (Solaris 2 5), SGI-IRIX 5 3 (or later), or DEC-Digital UNIX 3 2D (or later).

The databases of this invention may be downloaded via a 4×4 Gb+ FWSCSI-2, Fiber Link Raid Units 20Gb+, or 4 DAT Tape Drive. A CD ROM drive may also be acceptable.

The client machine may be, for example, a Macintosh™ (Apple Computer Inc. of Cupertino, Calif.), a PC, or a Unix workstation. It should also be TCP/IP capable with a Netscape Web Browser.

The network may include a 10-base-T connection, be TCP/IP capable, and provide access to Internet for HTML hyperlinks to NCBI.

4. Model of the Genomics Relational Database

Turning now to FIG. 3, a block diagram is shown of a physical data model 300 for a genomic relational database 146 in accordance with one embodiment of the present invention. As shown, this physical model 300 of data organization within the database 146 includes tables having as their primary keys (underlined) various pieces of data particularly relevant to a database of microbial biomolecular sequences. In addition, those tables which have a many-to-one relationship to one or more other tables also include primary key information (designated as foreign keys ("fk")) for those related tables. Of course, similar database models could be employed with biomolecular information from other sources such as plants, insects, mammals, etc.

The organization of data in the database 146 may also be represented by a logical data model 400, as depicted in FIG. 4. While the physical data model 300 represents the actual physical locations of various records within the tables of the relational database 146, the logical data model 400 is a conceptual representation of the data in the database 146. The foreign key information is not included in the logical data model 400, since it is redundant in the conceptual functioning of the database 146. It is included in the physical data model 300 since it is useful for a full understanding of how the database is organized and how the data is related and accessed. The structure and operation of a preferred embodiment of the database of the present invention is described below with reference to both the logical data model 400 and the physical data model 300, which contains tables and fields corresponding to the entities and attributes of the logical data model 400, in order to present both the conceptual and physical organization of this embodiment of the invention.

Each entity in data model 400 includes a name (e.g., "PA_Library"), a primary key attribute (or attributes) denoted by underlining, and a variable type (e.g., a floating point value, an integer, a character, etc.) indicated in a second column of each entity represented in FIG. 4. It should be understood, of course, that this embodiment of the invention is not limited to the data type specified in the second columns of the entities in database 400. The primary key(s) are also designated by underlining in the physical data model 300. In addition, physical data model 300 tables include a foreign key (or keys) denoted by a "fk" designation the second column of the tables. The lines between entites in database model 400 represent relationships between the primary key attributes and the various entities. For example, each sequence (identified by a SequenceID) in a PA_Sequences entity 404 belongs to a single library (identified by a LibraryID) in a PA_Library entity 402. But, each library in PA_Library entity 402 may have many different sequences represented in PA_Sequences entity 404. Thus, each entry in entity 402 (or record in corresponding table 302) may correspond to many entries in entity 404 (or records in corresponding table 304). This is referred to as a "one-to-many" relationship and is indicated by the branches at entity 404 on the line connecting entities 402 and 404.

The relationships between the entities may be optional or mandatory. Optional relationships are identified by a circle in the connecting relationship line. Thus, each record in entity 402 may have many corresponding records in entity 404. Mandatory relationships are indicated by a perpendicular line segment. Thus, for example, each sequence entry in entity 404 must belong to a library in entity 402. The triangular connection element between the PA_ExternalHit and the PA_GIAccession entities indicates a "dependent" identifying relationship, i.e., the child rows cannot exist without the parent. In this case, an entry in PA_ExternalHit may have one or more entries in PA_GIAccession and an entry in PA_GIAccession must have and be dependent on one and only one entry in PA_ExternalHit. The primary key attribute of the child in such a relationship is a composite key which is the primary key attribute of the parent (referenced as the foreign key in the corresponding physical data maodel 300,) as well as a primary key attribute of the child.

The physical data model 300 includes arrows between the tables representing the relationship of the foreign key (or keys) in a table to another table for which the foreign key(s) is a primary key.

PA_Library entity 402 in logical data model 400 has as its primary key attribute a LibraryID. This LibraryID uniquely specifies each library in the database 146. As explained above, each library is generated by cloning the nucleic acid from a single organism. Corresponding physical data model table 302 includes an OrganismID field which specifies the organism from which the library was derived. The logical data model PA_Library entity 402 does not include this attribute. Instead, the logical data model includes a separate PA_Organism entity 401 containing as its single attribute, OrganismID. Similarly, corresponding physical data model table 302 includes an HitDataSource field which identifies the external (i.e., GenBank) database source of the HitID used to annotate an ORF in a library. The logical data model PA_Library entity 402 does not include this attribute. Instead, the logical data model includes a separate PA_HitDB entity 403 containing as its single attribute, HitDataSource.

The PA_Library entity 402 also includes a PCTCGContent attribute, which provides the percentage of guanosine and cytosine (G and C) base pairs in a library. This information may be useful in determining physical and functional characteristics of sequences in the library. The ContigInSeqServer attribute is a yes (Y) or no (N) flag indicating if the nucleotide sequence for a particular Contig is available in the Sequence Database.

Next, a number of sequences attribute (NumSeqs) specifies the total number of basic sequences generated from the library and stored in the database. Number of ORFs (NumOrfs) and number of contigs (NumContigs) attributes specify the total number of open reading frames and contigs generated from the library's total complement of sequences, respectively. Next, an OrphanContigs field specifies the number of contigs from the library which had no match against a external database. The library description (LibDescription) and Comments attributes include short and longer descriptions, respectively, pertaining to a particular library record.

The entity 402 also includes a GenomeSize attribute which provides the size of a particular organism library, for instance, in Mbp. A Depth attribute provides information relating to the depth of coverage of an enterprise sequenced genome. The value of this attribute typically reflects the average depth of coverage. A Coverage attribute also provides the percentage coverage of a genome provided in the database of the present invention. For external databases, this value is generally 100%. For enterprise sequenced genomes, the value may be calculated, for example, by dividing the number of base pairs for all contigs by the organism's genome size.

PA_Sequences entity 404 includes as its primary key attribute a unique sequence ID (SequenceID) for each sequence in the database. A SequenceID refers to a particular genomic sequence generated during genome sequencing. As previously described, each genome sequence fragment is assigned a SequenceID following sequencing. The raw sequence is stored in the Sequence Database 144, while the associated SequenceID is stored in the PA_Sequences table of the relational genomic database 146. As indicated by the line connecting entity 404 to 402, each SequenceID belongs to a unique library. Corresponding physical data model table 304 includes a LibraryID, which is a foreign key to table 302 and a ContigID which is a foreign key to a PA_Contig table 306 (described below). These foreign keys are not represented as attributes in the corresponding logical data model entities, but are indicated by the relationship links between the entities. Entity 404 further includes a ContigStart attribute and a ContigEnd attribute. These specify the starting base pair and ending base pair, respectively, of the sequence within its contig. In one preferred convention, if a sequence is located at the 5' end of a contig, then the ContigStart field will be given the value zero. Data relating to these ContigStart and ContigEnd attributes is obtained during Contig Formation.

PA_Contig entity 406 includes as its primary key attribute a contig ID (ContigID) uniquely specifying each contig within the database. As noted above, a ContigID is assigned to an assembled sequence following the Contig Formation module of data processing. Whereas a SequenceID will remain constant throughout subsequent date processing, ContigIDs may change, particularly as new sequences are obtained which bridge multiple existing contigs into one. Corresponding table 306 has as a foreign key (shown in corresponding physical data model table 306) the LibraryID attribute from table 302. Other information derived from the Contig Formation module is also represented in this entity. For example, the entity also specifies the number of sequences within a particular contig (NumSeqs), and the length (Length) of the particular contig in number of base pairs. In addition, the number of open reading frames found within a particular contig (NumOrfs) is derived. Note that the NumSeqs and NumOrfs attributes in PA_Contig entity 406 have different meanings than the same named attributes in PA_Library entity 402. In entity 406 these attributes are counted within a single contig, while in entity 402 they are counted within an entire library.

Next, an entity 408 (denoted "PA_ContigLocus") has as its primary key attribute an open reading frame identifier (OrfID). OrfIDs and associated attributes of this enitiy are derived from the Gene Finding and Gene Clustering modules of the data processing. As described above, OrfIDs are assigned to ORFs located on the contigs assembled during Contig Formation by sequence matching with annotated sequences, for instance in GenBank. A ContigID field (as shown in corresponding physical data model table 308) is a foreign key to table 306. Note that each entry of entity 408 belongs to a unique contig from entity 406, as indicated by the relationship line connecting the entities. Next, a LocusType attribute defines the sequence entity type on a contig. For example, the LocusType field in the corresponding physical data model table 308 could contain a "O" to indicate that a particular sequence is an ORF or an "L" for a LUR. RelativePosition attribute of entity 408 specifies the relative position of the particular ORF under consideration within its contig. Thus, for example, the sixth open reading frame (from the 5' end) of a contig sequence would have the value six (6) in the relative position field of the corresponding physical data model table 308. Next, ContigStart and ContigEnd attributes specify the starting and ending position in base pairs of the open reading frame within the contig. Note that these attributes have a different meaning within PA_Sequences entity 404.

A number of sequences attribute (NumSeqs) specifies the number of basic sequences that are contained within the region of the contig denoted to be the open reading frame under consideration. Next, an EValue attribute specifies the E-value of the Hit of the open reading frame against the external database. As noted above, the lower the E-value the higher the probability that the Hit against the external database is meaningful. The E-value is used in the identification of ORFs during the sequence alignment processes (FASTX portion) of the Gene Finding module, and the annotation (FASTA) of ORFs.

A PSeqLength attribute provides the length of the protein sequence corresponding to an ORF. A Strand attribute indicates on which strand of the double stranded contig the ORF was found. The strand may be indicated, for example, by a "+" or a "−" appearing in the corresponding field of physical data model table 308. Next, a PctOfHit attribute indicates the percentage of the gene in the external database (i.e., GenBank) that is covered by an ORF on a contig. This value may be calculated by dividing the PSeqLength by the length of the Hit in the external database, and multiplying by 100.

A gene cluster ID field (GeneCluID) (as shown in corresponding physical data model table 308) is a foreign key to a gene cluster table 310 ("PA_GeneCluster") which will be described in more detail below. A HitID field and HitType field, shown in physical data model table 308, together represent a foreign key to an external hit table 316 (denoted "PA_ExternalHit"), which will be described in more detail below. Finally, a FCID field (as shown in corresponding physical data model table 308) is a foreign key to a functional classification table 322, and provides a functional classification ID number, according to a coded list of functional categories. In a preferred embodiment, these functional categories include, in ranked order: 1) Motility; 2) Virulence; 3) Transport; 4) Regulatory; 5) Macromolecule metabolism; 6) Small molecule metabolism; 7) Structural; and 8) Other. ORFs may be categorized based on keywords in their Hit Description. In a preferred embodiment, an ORF can only belong to one functional category, so if an ORF has keywords that fall into more than one category, the ORF is assigned to the category with the highest rank.

Gene cluster entity 410 includes as its primary key attribute the gene cluster ID (GeneCluID) mentioned above. This entity includes each gene cluster in the database. As noted above, such clusters are generated during a clustering step in the process of generating data to populate the database. Each gene cluster will include one or more OrfIDs specifying open reading frames determined based on homology and/or codon usage. Thus, an OrfID field (as shown in corresponding physical data model table 310) is a foreign key to the contig locus table 308 as indicated by the relationship between entities 410 and 408, and the connection between corresponding table 310 and 308, as described above. The ORFs in a gene cluster are identified by the Gene Cluster ID (referenced as a foreign key) in the PA_ContigLocus table 308. Each Gene Cluster is identified by a "Representative ORF". This is indicated by the OrfID (as a foreign key) in the PA_GeneCluster entity 410. The two arrows connecting these tables in the physical data model (and the two different connections depicted in the logical data model) reflect this relationship. One connection is a one-to-many from PA_GeneCluster to PA_ContigLocus, indicating that the Gene Cluster must have one or more ORFs in it, conversely, one ORF may belong to one and only one Gene Cluster. The other relationship is for the Representative ORF, i.e., a Gene Cluster must be identified by one and only one ORF, conversely, one ORF may represent one and only one Gene Cluster.

Gene cluster entity 410 also includes a NumLibs attribute indicating the number of libraries from among the total number of libraries represented in the database that belong to the cluster. An alternative way of reflecting this information, used in some embodiments of the present invention, is as the number of libraries in which a gene or ORF is not present (referred to as specificity). Thus, if three libraries are represented in the database and the gene cluster under consideration includes open reading frames from two of these three libraries, then the specificity could be set with a value of ⅓ or 0.333. Likewise, if the gene cluster includes open reading frames from only a single library, then the specificity value could be set at 0.667.

The physical data model 300 includes a gene cluster library table 312 ("PA_GeneCluLib") at the intersection of library table 302 and gene cluster table 310. Table 312 includes only two fields, a gene cluster ID and a library ID. Together these fields form the primary key of table 312. Of course, the library ID is a foreign key to table 302 and the gene cluster ID is a foreign key to table 310. Therefore the data contained in this table is redundant, and the table does not appear as and entity in the logical data model 400. Where, as here, two entities in a logical model have a many to many relationship between them, the situation is resolved in the physical model by an intersect table with the primary key made up of the primary keys from both the two tables (referenced as foreign key), and the relationships are one to many from both the parent tables to the intersect table. Table 312 appears this way in the physical data model 300. Table 312 is also used for quickly determining which libraries are represented within a particular gene cluster. Such information is useful in comparative genomics queries.

Another table present in the physical data model 300 but absent as an entity in the logical data model 400 is the PA_OrfSequences table 314, provided at the intersection of contig locus table 308 and sequences table 304. It includes as its primary key the combination of a sequence ID and an Orf ID. The sequence ID in table 314 is a foreign key from sequences table 304 and the Orf ID field in table 314 is a foreign key to table 308. As there may be many sequences within a given open reading frame, the mapping between records in table 308 and table 314 is a one-to-many mapping. Further, as a given sequence may be contained in multiple ORFs (typically no more than two), the mapping between records in table 304 and table 314 may be a one-to-many mapping. Table 314 is particularly useful for those screens displaying the sequences comprising an open reading frame (e.g., a Sequence Information Results page, such as shown in FIG. 6K). Because it contains redundant information, the table is not included in the logical data model 400.

The external hit entity 416 ("PA_ExternalHit") provides information about the hit from the external database giving rise to the open reading frames populating the contig locus entity 408. The information represented in this entity is developed from the Gene Finding stage of the process of data generation. Entity 416 includes as its primary key a combination of a HitID, which is a number provided by the external database, and a HitType, which is a single character also specified by the external database. In the case of GenBank, for example, the HitType might be a single letter such as "g" and the HitID might be an eight digit number. Entity 416 also includes a HitDescription field. Preferably, this field includes a short summary of descriptive information about the hit taken from the external database. An example of a HitDescription includes "xylose receptor." A HitOrgID field (as shown in corresponding physical data model 300) is a foreign key to a PA_HitOrganism entity 420. This field identifies each of the organisms that exist within an external database, such as GenPept. Because multiple open reading frames for the database may hit the same record in an external database, the relationship between records in entity 416 and entity 408 is a one to many relationship.

A PA_GIAccession entity 418 specifies as a primary key attribute the accession number (Accession) of an external database (e.g., GenBank) sequence corresponding to an external hit of interest. As shown in corresponding physical data model table 318, the table has a HitID which is both a primary key and foreign key to the external hit table 316. Together these attributes form the primary key of table 318. PA_GIAccession contains a list of unique accession numbers assigned to each record submitted to GenBank. Sequences with different GI numbers are accessed under the same accession number if the sequences are the same.

A PA_Hit Organism entity 420 is also related to the PA_External Hit entity 416, and includes a HitOrgID as its primary key which identifies each of the organisms that exist within an external database, such as GenPept. This entity also has a HitOrganism attribute which identifies the organism from which an external genomic library is drawn. In the case of GenBank, the HitOrganism field identifies the organism specified by the characters following the "gi" in the GI number.

A PA_FuncClass entity 422 includes a FCID attribute as its primary key. The FCID provides a functional classification ID number, according to a coded list of functional categories, an example of which is described above. A Name attribute provides the name of the functional classification corresponding to a particular FCID, and a SortOrder attribute provides the order in which the functional classifications should be displayed to a user in a graphical user interface according to a preferred embodiment of the invention.

Finally, a version entity 424 (and corresponding table 324 of physical data model 300) includes as its primary key attribute a software product description. Entity 424 also includes a software version attribute and a data release month and year attribute. The data release attribute is necessary to specify which data set is populating the database currently in use. It is possible that a given version of the software product will be updated with multiple data releases. The information respresented in entity 424, and contained in corresponding table 324, may be displayed on each page of the graphical user interface.

5. Graphical User Interface for Genomic Sequences Database

In a preferred embodiment, the invention is provided together with a suite of functions made available to users through a collection of user interface screens (e.g., HTML pages). Typically, the interface will have a main menu page from which various lines of query can be followed. Of particular relevance to the present invention is a main menu screen which allows users to travel toward information regarding Comparative Genomics and Electronic Southerns.

FIG. 5A presents one such main menu page 500 which may be employed in a database having genomic sequences contained therein. As shown, menu page 500 includes buttons for accessing the following lines of query: Comparative Genomics (button 504), Organisms (button 506), Electronic Southerns (button 508), Gene List (button 510), Gene Locus (button 512) and Sequence Database (button 514).

If a user selects button 504, he or she will receive a Comparative Genomics Query screen (such as shown in FIG. 6A). In a preferred embodiment, this screen 600 displays lists of target organisms and background organisms. By making appropriate selections from each list a user may look up genes common to a set of organisms or unique to an organism or set of organisms. This line of query is described in more detail below.

Should the user select button 506 (Organisms), he or she will receive an Organism Information Results screen 550 (such as shown in FIG. 5B). In a preferred embodiment, this screen 550 lists each organism library available in the database of the present invention, for instance, in alphabetical order. In a specific embodiment, text lines on the screen display each library's name, a brief description of the organism from which the library is derived, the number of usable sequences, the number of assembled contigs for that library, the number of ORFs in the library, the approximate size of the library, the depth and coverage of the of the library relative to the entire genome of the corresponding organism, and the GC content of the library. For public genomic data, N/A may be displayed in the Usable and Depth column, and the number of contigs is generally one, indicating a completely sequenced genome. This screen may include links to other screens displaying other information relating, for example, to a particular library or ORF. For example, selecting an underlined link in the Library column may return an Organism Details screen (not shown), which provides additional information about the selected library.

When the system determines that button 508 (Electronic Sourtherns, analogous to the Southern blot laboratory technique) has been selected, it will allow the user to identify libraries in which a given gene or ORF exists. For example, a user may enter an OrfID in an Electronic Southern query screen (such as shown in FIG. 7A). The system may then return all libraries that contain members of the ORF's Gene Cluster in an Electronic Southern Results screen (such as shown in FIG. 7B). This line of query is described in more detail below.

If the user should select the button 510 (Gene List), the database system will return a Gene List Query screen, such as shown in FIG. 5C. Screen 560 displays a list of organism libraries and allows the user to view all ORFs from a library by selecting that library from the list. The Gene List Results screen, shown in FIG. 5D, provides a list of all ORFs for the selected library 570, preferably together with other associated information. From the results screen, the user will have the option of selecting links to various other screens displaying related information. In the specific embodiment depicted in FIG. 5D, links are provided via the ORF ID, Hit ID, E-Value and NumLibs fields.

The user may also select button 512 (Gene Locus) from the main menu screen 500 to have the system return the Gene Locus Query screen 580, shown in FIG. 5E. Query screen 580 allows a user to define search criteria and select an organism library as the subject of the search. The Gene Locus Results screen 590, shown in FIG. 5F, then displays the relative location of an ORF on a contig to its neighboring ORFs.

The Gene List and Gene Locus features of the database system are described in more detail in a companion patent application Ser. No. 08/856,647 (attorney docket no. ICYTP003), filed concurrently herewith and previously incorporated by reference.

Finally, when the system determines that the user has selected button 512 (Sequence Database), it allows the user to retrieve actual amino acid and/or nucleotide sequences for given SequenceIDs. It also allows the user to perform sequence alignment searches (e.g., BLAST, FASTA) against various sequence databases (typically external databases), and to assemble nucleotide sequence fragments from a cluster and view how they overlap with each other. In addition, a user may use this feature to compare microbial sequences to sequences from other organismal families, such as plants and animals, including human sequences. The Sequence Database also allows a user to perform multiple sequence alignments using the Clustal W algorithm, a multiple sequence alignment program for DNA or protein. Further information on the Clustal W program is available on the World Wide Web at www.csc.fi/molbio/progs/clustalw/dot.imgen. In this way, a user may compare more than two sequences in a single operation.

Preferably, the user interface employed with this invention possesses similar attributes to interfaces for other sequence databases (besides a genomic database). Examples of other databases including similar interfaces might include (1) a general purpose short sequence database (containing for example ESTs as in the case of Incyte Pharmaceutical's LifeSeq™ database and interface), (2) a full-length sequences database (such as Incyte Pharmaceutical's LifeSeq-FL™ database and interface), and a plant genomic sequences database (such as Incyte Pharmaceutical's PhytoSeq™ database and interface). The "look and feel" of each of these databases preferably will resemble one another. For example, each might contain a commonly formatted collection of query buttons as shown as buttons 504, 506, 508, 510, and 512 in the main menu page of FIG. 5. As a result the system may bring one of multiple available "query" screens, each commonly formatted to allow the user to formulate his or her query. Upon execution of this query, the system may present an appropriate results screen (again of common format) presenting the results of the executed query.

By providing these features as a common interface spanning multiple sequence databases, users familiar with one database interface can quickly learn to navigate through related databases. Thus, they will be able to leverage their knowledge of formulating appropriate queries and locating desired sequence information obtained from working with an initial database (e.g., the LifeSeq™ database). This is the motivation behind providing any standard. In this case, the inventors have recognized that sequence database interfaces currently available have disparate looks and feels. By standardizing the look and feel of multiple sequence databases, the inventors have brought a needed consistency to the sequence database industry.

6. The Comparative Genomics User Interface

Comparative Genomics is a feature of the enterprise database which allows a user to compare the sequence data of sets of different organism types. Comparative searches may be formulated in a number of ways using the Comparative Genomics feature. Genes common to a set of organisms may be identified through a "commonality" query. Comparative Genomics may also be used to locate genes unique to one of a set of organisms. This is referred to as a "subtraction" query. Comparative genomics is performed on the basis of Gene Clusters.

In a preferred embodiment, the Comparative Genomics feature is accessed by clicking on the Comparative Genomics button 504 in the main menu Microbial Genomics screen 500, illustrated in FIG. 5A. This selection returns the Comparative Genomics Query screen 600, illustrated in FIG. 6A. A user may define the parameters of the comparison to be done by selecting one or more libraries listed in the Target Organism box 602, and from none to all of the libraries listed in the Background Organism box 604 in screen 600. Each line in the Target and Background library selection boxes displays the library's name, the full name of the organism, and the approximate size of the organism's genome.

For example, to perform a commonality query, a user would select libraries only in the Target Organism selection box 602. No libraries would be selected from the Background Organism selection box 604. The Search button (not shown) would then be selected. Buttons 605 are provided in order to provided direct access to other aspects of the database system. A Clear button (not shown) may also be provided in order to clear previous selections.

The Comparative Genomics Results screen 610, illustrated in FIG. 6B, would display those Gene Clusters containing members from the set of selected Target libraries. Because gene clusters may be composed of multiple ORFs, the ORF with the best match for its annotating GI (GenBank Identifier) is designated as the representative ORF, and its associated annotation is displayed as the description for a given cluster. In the preferred embodiment depicted in FIG. 6B, the Hit ID, Hit Description, Hit Organism, E-value, and NumLibs for the representative ORF are displayed on the one-line gene description.

Similarly, a subtraction query may be performed by selecting one or more libraries in both the Target and Background Organism boxes 602, 604. The results screen 610 will display only Gene Clusters common to the selected Target libraries, excluding Gene Clusters which are also common to Background libraries.

In addition, the Comparative Genomics feature provides the ability for the user to view a complete list of the gene clusters for a given organism library by selecting only that library in the Target Box 602, and no libraries in the Background Box 604 of the query screen 600. While this is not a comparative search, it does provide a useful presentation of information in the library to the user (i.e., as gene clusters).

FIG. 6C presents a process flow diagram of a system module which responds to comparative genomics queries formulated by a user of the system. A process 650 begins at 652 and in a step 654 displays a Comparative Genomics Query page such as screen 600 shown in FIG. 6A. Next, a decision step 656 determines whether the user has initiated a comparative genomics query by, for example, selecting a search button. If not, a decision step 658 determines whether the user has selected a link to a different page or exited the program. If the user has done one of these, the linked page is displayed if necessary at a step 660. Thereafter the process is completed at 670. If the user has not selected a link to a different page or exited the program, process control returns to step 654 from decision step 658.

It should be noted that the system allows the user to exit from the comparative genomics query mode at any time. The user may take this route by exiting the program or selecting a screen unrelated to the comparative genomics query from among the various buttons 605 provided. This option is depicted at a decision step 658 where the system determines whether the user has selected a link to another screen or exited the program. For purposes of illustration, this step is performed after decision step 656 is answered in the negative. Process control is shown returning to step 654 when step 658 is answered in the negative. If decision step 658 is answered in the affirmative (i.e., the user elected to leave the comparative genomics query mode), the system performs the appropriate action, for example, displaying a query screen from another of the database system's mode of inquiry, at a step 660.

The loop including steps 656, 658 and 654 is provided primarily for purposes of illustration. It should be understood that the invention is not limited to this arrangement (or any polling procedure) and may merely await receipt of an appropriate event from the user interface, for example. Moreover, this step could equally well have been depicted anywhere in the flow of process 650.

It should also be noted that various links (preferably HTML links) to additional related screens may also be provided in addition to the buttons 605, such as those illustrated in record 612 of FIG. 6B (Comparative Genomics Results screen). As noted above, a user may select a Hypertext link (e.g., a highlighted entry) in order to access linked information in the database. In one embodiment, the following Hypertext links, with their associated linked information, are provided: Hit_ID, displays an external database interface page (e.g., Entrez for GenBank; Expasy for Swiss Prot) with information relating to that project; E-Value, displays sequence alignment (e.g., FASTA) search results for the representative ORF and its best matching GI (GenBank); and NumLibs, displays a Electronic Southern results for similar ORFs (see below for further details on Electronic Southerns (alternative embodiments might use a Specificity attribute, as defined above).

If, on the other hand, decision step 656 determines that the user has in fact initiated a comparative genomics query, then the system identifies those libraries selected as target libraries and those libraries selected as background libraries in a step 662. As described above with reference to FIG. 6A, Comparative Genomics Query page 600 includes a target organism window 602 and a background organism window 604. Preferably, each of these windows displays all organisms providing libraries in the database. The user can then select any number of target organisms and any number of background organisms. This information is used by the system in step 662.

After the system has identified the appropriate background and target libraries in step 662, at step 664 it identifies all gene clusters that exist within the intersection of all target libraries and not in the union of all background libraries. One example of this situation is illustrated by set diagram 670 in FIG. 6D where the intersection of two target libraries, T1 and T2, is bounded by a dotted curve 671. The identified gene clusters resulting from the comparative genomics query in this example would be contained within a hatched region 672 which includes all gene clusters within region 671 and not in background libraries B1 and B2.

After the system has selected the appropriate gene clusters at step 664, it returns a Comparative Genomics Results page (e.g., 610 in FIG. 6B) displaying the various hits remaining after the comparison at a step 666.

Thereafter, at a step 667, the system determines whether the user has returned to the comparative genomics query page to do another search. If so, process control return to decision step 654 where execution continues as described above. If not, process control is directed to a decision step 668 which determines whether the user has taken an action that links to another screen or exits the program. If the user has so acted, the appropriate action is taken at step 660 as described above. If the user has not acted, the system simply continues to displaying the results page as indicated at a step 669. While displaying the results page, the system the system monitors events to determine whether the user has acted in accordance with steps 667 or 668.

The view definitions for the above-described embodiment of the comparative genomics feature of the present invention are as follows:

CREATE OR REPLACE VIEW PA_Libraries_V AS

SELECT    lib.LibraryID,
             lib.OrganismID,
             lib.PctGCContent,
             lib.HitDataSource,
             lib.NumSeqs,
             lib.NumOrfs,
             lib.NumContigs,
             lib.OrphanContigs,
             lib.LibDescription,
             lib.Comments,
             lib.GenomeSize, -continued

```
                lib.Depth,
                lib.Coverage
FROM            PA_Library lib
/
CREATE OR REPLACE VIEW PA_GeneClusterLibraries_V AS SELECT  gclulib.GeneCluID,
        gclulib.LibraryID
FROM    PA_GeneCluLib gclulib
CREATE OR REPLACE VIEW PA_GeneComparison_V AS SELECT DISTINCT gclulib.GeneCluID,
                contlo.HitID,
                contlo.HitType,
                contlo.ContigID,
                contlo.NumSeqs,
                decode(NVL(contlo.HitID,0),0,decode(contlo.Locus-
                Type,'O','INCYTE','L','LUR'),
                            exthit.HitDesription) HitDescription,
                lib.HitDataSource,
                hitorg.HitOrganism,
                contlo.OrfID,
                contlo.EValue,
                geneclu.NumLibs
FROM            PA_ExternalHit exthit,
                PA_ContigLocus contlo,
                PA_GeneCluster geneclu,
                PA_HitOrganism hitorg,
                PA_Library lib,
                PA_GeneCluLib gclulib
WHERE           gclulib.LibraryID = lib.LibraryID
AND             gclulib.GeneCluID = geneclu.GeneCluID
AND             geneclu.OrfID = contlo.OrfID
AND             contlo.LocusType = 'O'
AND             contlo.HitID = exthit.HitID(+)
AND             contlo.HitType = exthit.HitType(+)
AND             exthit.HitOrgID = hitorg.HitOrgID(+)
/
```

A particular view is created in this embodiment using SQL select statements. An example of a select statement for a hypothetical comparative genomics query where two target libraries, "ECOLI01" and "EFAECA01" have been selected as targets, and "MPNEUM01" and "SAUREU01" have been selected as background libraries:

```
                    Comparative Genomics Query
SELECT   LibraryID,
         substr(LibDescription,1,80)
FROM     PA_Libraries_V
ORDER BY LibraryID
Comparative Genomics SELECT   count(*)
FROM     PA_Libraries_V
SELECT   DISTINCT nvl(gc.HitID,99999999),
         gc.HitType,
         nvl(gc.HitDescription,''),
         gc.HitDataSource,
         nvl(substr(gc.HitOrganism,1,15),''),
         gc.OrfID,
         nvl(gc.EValue,0),
         gc.NumLibs,
         gc.ContigID,
         gc.NumSeqs
FROM     PA_GeneComparison_V gc
WHERE    gc.GeneCluID IN (SELECT gcl1.GeneCluID
                          FROM   PA_GeneCluster-
                                 Libraries_V gcl1
                          WHERE  gcl1.LibraryID IN
                                 ('ECOLI01', 'EFAECA01')
                          AND    gcl1.GeneCluID =
                                 gcl1.GeneCluID
                          GROUP BY gcl1.GeneCluID
                          HAVING COUNT(*) = 2)
```

```
                    Comparative Genomics Query
AND      gc.GeneCluID NOT IN (SELECT DISTINCT
         gcl2.GeneCluID
                          FROM   PA_GeneCluster-
                                 Libraries_V gcl2
                          WHERE  gcl2.LibraryID IN
                                 ('MPNEUM01',
                                 'SAUREU01')
                          AND    gcl2.GeneCluID = gcl2.-
                                 GeneCluID)
ORDER BY nvl(gc.HitID,99999999)
```

As noted above, if a user desired to search for genes common to two or more organisms, he or she would list the libraries associated with those organisms in the target organism field 602 of the Comparative Genomics Query page 600. No libraries would be entered in the background library field 604. The result would include only genes (represented as gene clusters in a preferred embodiment) found in all target libraries. To perform a subtraction query, the user selects libraries in both the target and background fields. The displayed results include those genes found in all the target libraries but none of the background ones. To look for genes specific to a single organism, the user selects that organism from among the target libraries field and selects every other organism available in the background libraries field.

Example 1

Searching for Genes Unique to a Single Organism

Based on the foregoing, it can be seen that in order to look for genes unique to a single organism, the user would select that organism among those listed in the Target library box 602 of Comparative Genomics Query screen 600 and select every other organism available in the Background library box 604. An example of this type of Comparative Genomics search is shown in FIGS. 6E through 6P. This example demonstrates the functionality of the comparative genomics feature of one embodiment of the database system of the present invention.

In the this example, a subtraction query is performed. *Streptococcus pyogenes* ("Strep") was selected as the Target Organism and *Haemophilus influenzae* ("Hflu") and *Mycoplasma genitalium* ("Myco") were selected as the Background Organisms in a Comparative Genomics Query screen 600, depicted in FIG. 6E. Once these organisms had been selected by the user by clicking on their respective lines in the Target Organism 602 and Background Organism 604 boxes, the user clicked on the search button 606 to initiate the search.

The results of the search were then displayed in the Comparative Genomics Results screen 610, illustrated in FIG. 6F (in truncated form). The results are displayed as Gene Clusters and not as individual ORFs. Because a Gene Cluster may be composed of multiple ORFs, the ORF with the lowest P-value (in this embodiment) is designated as the representative ORF, and its associated annotation is displayed as the description for the given gene. In this particular embodiment, the Hit ID, Hit Description, Hit Source, P-Value, and Specificity of the representative ORF for each Gene Cluster returned by the search were displayed in a one line entry for each Gene Cluster on the results screen.

The results of the present example show all the hits, that is all representative ORFs, appearing in Strep, but not in Hflu or Myco. This result is confirmed by the fact that the specificity for all of the hits is 0.6667, which indicates that the displayed ORFs are present in only one of the three organisms selected (i.e., not present in two thirds of the organisms selected).

Continuing with the present example, the user may scroll between the results screens to locate Gene Clusters associated with a protein of interest. In the case of Strep, one protein of particular interest is the enzyme hyaluronidase, which is responsible for the breakdown of connective tissues, including skin, in order to provide the organism entry into a biological host. In this example, there were three separate hits listed for the enzyme hyaluronidase in lines 611, 612 and 613. These hits may be identified by the functional description found in the Hit Description field of each entry. Because this was a subtractive search with all libraries for organisms other than the target selected as background, each of the three separate hits listed for hyaluronidase in the Comparative Genomics Results screen 610 represents a cluster unique to Strep.

In order to further explore the character of the identified Strep hyaluronidase ORFs, the user may click on the Hit ID for the cluster corresponding to that ORF. In the present example, the user clicked on Hit ID gl44861 611, the first instance of hyaluronidase in the results screen in the present example. This selection returned the Electronic Southern Results screen 615, as illustrated in FIG. 6G. In this example, the Electronic Southern Results screen 615 showed a single line entry 616 which identifies the name of the library, its description, the number of copies, that is the number of ORFs corresponding to the Cluster for gl44861, and the ORF ID. In the present instance, the cluster comprised only a single ORF. Therefore, the ORF ID listed in entry 616 is for that one ORF. Where more than one related ORF from the same library is comprised within the same Gene Cluster, the ORF with the best P-value (or lowest ID number if the P-values are the same) would be displayed in the ORF ID column of entry 616.

To obtain further information on Cluster for gl44861, the user clicked on the number of copies field 617 in entry 616, which returned the Organism Gene Copies screen 618, as illustrated in FIG. 6H. In entry 619, the screen shows all ORFs in Cluster Hit ID gl44861. By clicking on ORF ID 620 in row 70, the user returned the Gene Locus Information screen 621, as illustrated in FIG. 6I. This screen showed the relative position of the hyaluronidase cluster for gl44861 on its associated contig, SPc00596. The ORF ID field 622 of the results screen 621 showed that contig SPc00596 contains five (5) ORFs and two (2) LURs, listed in the order in which they exist on the contig. The results also showed that cluster for gl44861 is in the middle of the contig, which is a good indication that it represents a complete sequence of the gene. By clicking on the P-value 624 in row 623 on the Gene Locus Information screen 621, the user returned the BLAST Search Results screen 625, as illustrated in FIG. 6J. The BLAST Search Results screen 625 shows data which indicates how well the hyaluronidase sequences on the contig (Spc00596) align with those in an external (e.g., public) database.

Next, by clicking on the Sequence Info button in a BLAST Search Form screen (not shown), the Sequence Information Results screen 626 was returned, as illustrated in FIG. 6K. This screen lists the specific sequences in the genomic library for this organism which are within the portion of contig SPc00596 that relates to ORF SP001074. In this particular example, there were 14 individual sequences which related to ORF SP001074.

From the Sequence Information Results screen 626, the user has several options which may be exercised by clicking on the various buttons available. For instance, the user could click on the assembly button 627 in order to show additional information relating to ORF SP001074. In this particular example, this option was not exercised.

Instead, in order to investigate other hyaluronidase clusters identified previously in the Comparative Genomics search, the user clicked on the Main Menu button 628 in the Sequence Information Results screen 626 to return to the Microbial Genetics main menu screen shown in FIG. 6A, and then advanced to the Comparative Genomics Results screen shown in FIG. 6B. The user then clicked on Hit ID g437705 612, the second instance of hyaluronidase in the results screen in the present example This selection returned an Electronic Southern Results screen (not shown). As with the first hyaluronidase hit, the Electronic Southern Results screen showed that the cluster comprised only a single ORF.

Then, returning to the Comparative Genomics Results screen shown in FIG. 6B, as described above, the user clicked on the third Hit ID g881507 613, which returned the Electronic Southern Results screen 630 shown in FIG. 6L. In this instance, the copies column 631 in entry 632 showed that there are six contigs in Cluster g881507. By clicking on the number of copies 631, the Organism Gene Copies screen 633 illustrated in FIG. 6M is returned. This screen identifies the six ORFs which are grouped within the selected cluster.

Further information regarding these ORFs and their respective contigs may be obtained by clicking on the various HTML links available in the Organism Gene Copies screen 633. For instance, it may be interesting to further investigate those ORFs with the lowest P-Values, since those are less likely to be fully described in available databases. In the present example, the P-values for ORF Ids SP001043 634 and SP000709 635 were the highest for any of the six ORFs. The user clicked on ORF ID SP001043 634, returning the Gene Locus Information screen 636 illustrated in FIG. 6N. Line 637 of the Gene Locus Information screen 636 showed that ORF ID SP001043 is at the beginning of contig Spc00591. This may indicate that the ORF represents an incomplete copy of the hyaluronidase gene. At this point, the user clicked on the P-Value HTML link 638 in line 637 to return the BLAST Search Results screen showing the alignment of contig SPc00591 with the associated GenBank sequence (not shown). In this example, the results of the BLAST showed that the beginning of the contig overlaps with the end of the protein.

In order to investigate other ORFs in this cluster, the user clicked on HTML links to return to the Organism Gene copy screen 633, shown in FIG. 6M, and then clicked on ORF ID SP000709 635, to return the Gene Locus Information screen 639 associated with that ORF, shown in FIG. 6O. As shown in FIG. 6O, ORF ID SP000709's contig contained only that ORF and a LUR. Therefore, as with ORF SP001043, this ORF is suspect and likely does not contain the entire sequence for the hyaluronidase gene. By clicking on the P-Value 641 in line 640, the BLAST Search Results screen for ORF SP000709 was returned. The BLAST results (not shown) showed that the end of the contig SPc00495 overlaps the beginning of the protein. From this data, it may be concluded that ORF Ids SP001043 and SP000709 are two halves of the same gene and that deeper sequencing may bring these two halves together into a single ORF.

Gene Locus information for the remaining four ORFs may be obtained by following the equivalent steps previously outlined. In this example, the P-Values were very low (the lower P-value representing the higher confidence value) for these four remaining ORFs. FIG. 6P shows a representative example Gene Locus Information screen 642 for one of these remaining ORFs, that being ORF ID SP001088 as shown in row 643 of the figure. Since the ORF is located in the middle of its contig, it likely represents the entire coding sequence for the hyaluronidase gene.

FIG. 6Q shows a representation of the Strep genome 680 showing the eight ORFs coding for hyaluronidase from the preceding example. As described in the example, the eight ORFs were grouped in three gene clusters. The gene cluster corresponding to each ORF is indicated in the figure by the annotations H1, H2 and H3 (H for "Hit"). As noted, two of these H3 ORFs may actually be a single ORF that will come together with deeper sequencing.

The Comparative Genomics feature of the database of the present invention allows a user to electronically compare the sequence data of sets of different organisms. Some preferred and specific embodiments of the comparative genomics feature have been described. However, those of skill in the art will recognize that comparative genomics may be implemented in a database system of the present invention in other ways which do not depart from the spirit and scope of the invention.

7. Electronic Southern Graphical User Interface

Electronic Southerns are useful for identifying genomic libraries in which a given gene or ORF exists. A Southern analysis is a conventional molecular biology technique is a in which a nucleic acid of known sequence is used to identify matching (complementary) sequences in a sample of nucleic acid to be analyzed. Typically, DNA which has been separated on an electrophoretic gel is denatured is transferred to a membrane by contacting the membrane with the gel and allowing the DNA to bind to the membrane. The membrane then contains a replica of the bands of DNA separated in the gel. The membrane may then be washed with a solution containing labeled (e.g., radioactively) DNA or RNA probes. The probes will hybridize to any complementary sequence samples on the membrane, and the location of these hybridized samples on the membrane and the corresponding gel may be detected by autoradiography. Where the sequences of the labeled probes are known, the technique will provide the researcher with information about likely sequences of his or her unknown. Alternatively, in the absence of sequence data about the known samples, the image may simply tell the researcher which organisms, tissues, clones, etc. (each associated with a given known sample) hybridized to the unknown sample. One purpose of the Electronic Southern analysis described here is to allow similar types of information to be obtained electronically from nucleic acid sequence information stored in a database. For instance, like their laboratory counterparts, Electronic Southerns may be used to locate homologous matches between a "probe" DNA sequence and a large number of DNA sequences in one or more libraries. In a preferred embodiment of the present invention, such homology analysis is based on Gene Clustering.

A preferred embodiment of a graphical user interface which provides access to the various tools of the present database is shown in FIG. 5A. To perform an Electronic Southern analysis, a user selects the Electronic Southern category by clicking on the Electronic Southern button 508 in the main menu screen 500. This will display the Electronic Southern query screen 700, which is used to define the selection criteria for the Electronic Southern results. To perform an Electronic Southern analysis, the user selects a search category from a pull-down menu which is displayed when the user clicks on the search Type box 702. Search subjects in the menu may include GI (GenBank identifier—a unique number assigned to protein and nucleotide sequences in the GenBank database), Accession Number (a unique number assigned to each submission of a nucleotide or protein record to GenBank; may relate to multiple GIs), ORF ID (a unique identifier for an Open Reading Frame on a contig in a given organism library), GI Description (annotation describing the sequence of a submitted GenBank entry), and others. The user also enters a search term corresponding to the search Type in the Value text box 704 provided on the screen.

For example, searching may be done using the GenBank identifier search Type for which a nucleotide or protein GI number is entered in the search term Value text box. Or the search may be conducted using the Accession number Type and entering a GenBank Accession number in the search term Value text box. In each case, the Electronic Southern Results screen 710, illustrated in FIG. 7B, will display all libraries, typically in alphabetical order, that contain Gene Clusters with ORFs matching the sequence associated with the search term entered in the Value text box 704 on the query screen 700. As another example, when searching is done using the ORF ID category, an ORF ID number is entered in the search term Value text box. In this case, the Electronic Southern Results screen will display all libraries, typically in alphabetical order, that contain members of the Gene Cluster of the ORF which corresponds to the ORF ID entered in the query screen Value text box.

FIG. 7C presents a process flow 750 for conducting an Electronic Southern analysis in accordance with one preferred embodiment of the present invention. As shown in FIG. 7C, the process 750 begins at 752 and then in a step 754, the system displays an Electronic Southern Query screen, such as screen 700 illustrated in FIG. 7A. As noted above, such screens allow the user to enter information relating to a specific sequence. At step 756, the system receives the user's query entry. Next, at decision step 758, the system determines whether the query entry is in the form of an internal open reading frame ID (ORF ID) or if it relates to an external database ID (i.e., a GI number). If the entry is in the form of an ORF ID, then the system displays an Electronic Southern Results screen, such as screen 710 illustrated in FIG. 7B, listing all libraries containing members of the entered ORF's Gene Cluster, at step 760. Alternatively, if the query entry takes the form of external database record identifier, then the system displays an Electronic Southern Results page listing all libraries containing Gene Clusters with open reading frames matching the external database record at step 762.

As noted above, in a preferred embodiment, Electronic Southern results are displayed as Gene Clusters in the Electronic Southern Results screen 710. Results are displayed as Gene Clusters. If the search is based on ORF ID (as depicted in FIGS. 7A and 7B), the top of the screen displays the selected ORF ID as well as the Hit ID and Hit Description, when there is a match. Alternatively, if the search is based on GI number, the top of the screen displays the selected GI number and the Hit Description. When the search is based on Accession number, no additional information appears on the top of the page. Each line 712 displays the library name, library description and size and number of copies (or paralogs) found in that particular library. In rare cases, related ORFs may appear more than once within the library. This means that multiple related ORFs in the same library are in same Gene Cluster. When this occurs, the total number of ORFs from that library will appear in the Copies (or Paralogs) column. The ORF with the best E-value will be displayed in the ORF ID column.

Regardless of which version of the Southern results page is displayed, the user now knows which libraries within the internal database likely contain sequences matching his or her selected sequence. From this information, the user can determine which organisms like harbor genes similar to those he or she is investigating. He or she can also further analyze the gene clusters that match his or her selected sequence. To do this, the user may select a specific HTML link in a field from one of the records displayed in the Southern results page. In process 750, this is depicted at a decision step 766 where the system determines whether the user has selected an entry from the "Library", "Copies"/ "Paralogs," or "ORF ID" fields of the results screen.

If the user has not selected one of these fields, the system determines whether the user has alternatively selected another link to a different page or exited the program at a decision step 768. If the user has not done one of these functions, the system simply maintains the current display (step 770). It should be noted that the system allows the user to exit from the Southern query mode at any time. The user may take this route by exiting the program or selecting a screen unrelated to the Southern query from among the various buttons provided in the query and results screens. The loop including steps 766, 768 and 770 is provided primarily for purposes of illustration. It should be understood that the invention is not limited to this arrangement (or any polling procedure) and may merely await receipt of an appropriate event from the user interface, for example. Moreover, this step could equally well have been depicted anywhere in the flow of process 750. If, on the other hand, the user has selected another page or exited the program at step 768, the system displays the linked page, if necessary, at step 772, and the process is completed at step 774.

If, at decision step 766, the system determines that the user has selected an entry from the "Library," "Copies"/ "Paralogs," or "ORF ID" fields of the results screen by clicking on an appropriate hypertext link, corresponding Organism Details (step 776), Organism Gene Copies (step 778) or Gene Locus Information (step 780) pages, respectively, are displayed. The Organism Details screen displays descriptive information about the selected library. The Organism Gene Copies screen displays the related ORFs within the same library. And the Gene Locus Information screen displays the relative location of an ORF on a contig to its neighboring ORFs. If the search is based on GI, selecting the GI hypertext link will return the Entrez Report for the associated ORF. Following the display of any of these pages, the process is completed at step 774.

The view definitions for the above-described embodiment of the electronic southern feature of the present invention are as follows:

```
CREATE OR REPLACE VIEW PA_OrfLibraries_V AS
SELECT    contlo.GeneCluID,
          contlo.OrfID,
          lib.LibraryID,
          lib.LibDescription
FROM      PA_Contig cont,
          PA_Library lib,
          PA_ContigLocus contlo
WHERE     contlo.ContigID = cont.ContigID
AND       cont.LibraryID = lib.LibraryID
/
```

```
CREATE OR REPLACE VIEW PA_OrfHitDescription_V AS
SELECT    contlo.OrfID,
          contlo.HitID,
          contlo.Hitlype,
          decode(NVL(contlo.HitID,0),0,decode(contlo.Locus-
          Type,'O','INCYTE',exthit.HitDescription)
          HitDescription,
          lib.HitDataSource
FROM      PA_ExternalHit exthit,
          PA_Contig cont,
          PA_Library lib,
          PA_ContigLocus contlo
WHERE     contlo.HitID = exthit.HitID(+)
AND       contlo.HitType = exthit.HitType(+)
AND       contlo.ContigID = cont.ContigID
AND       cont.LibraryID = lib.LibraryID
/
CREATE OR REPLACE VIEW PA_OrfHitGeneClusters_V AS
SELECT    contlo.GeneCluID,
          contlo.OrfID,
          contlo.HitID,
          contlo.HitType
FROM      PA_ContigLocus contlo
/
CREATE OR REPLACE VIEW PA_AccGeneClusters_V AS
SELECT    contlo.GeneCluID,
          giacc.Accession
FROM      PA_ContigLocus contlo,
          PA_GIAccession giacc
WHERE     giacc.HitID = contlo.HitID
/
```

The particular views are created in this embodiment using SQL select statements in accordance with the following, for search based on GI number, Accession number, and ORF ID, respectively:

```
                       Southerns
**BY GI
SELECT    NVL(HitDescription,''),
          NVL(HitDataSource,'')
FROM      PA_OrfHitDescription_V
WHERE     HitType = 'g'
AND       HitID = 345145
GROUP BY  HitDescription,
          HitDataSource
SELECT    LibraryID,
          LibDescription,
          count(*)
FROM      PA_OrfLibraries_V
WHERE     GeneCluID in (SELECTGeneCluID
                        FROM PA_OrfHitGeneClusters_V
                        WHERE HitType ='g'
GROUP BY  LibraryID,
          LibDescription
ORDER BY  LibraryID
SELECT    DISTINCT OrfID
FROM      PA_OrfLibraries_V
WHERE     GeneCluID IN (SELECT GeneCluID
                        FROM PA_OrfHitGeneClusters_V
                        WHERE HitType = 'g'
                        AND HitID = 345145)
ORDER BY OrfID
**BY Accession
SELECT    LibraryID,
          LibDescription,
          count(*)
FROM      PA_OrfLibraries_V
WHERE     GeneCluID in (SELECT GeneCluID
                        FROM PA_AccGeneClusters_V
                        WHERE Accession = 'A11530')
GROUP BY  LibraryID,
```

-continued

Southerns

|  | LibDescription |
|---|---|
| ORDER BY | LibraryID |
| SELECT | DISTINCT OrfID |
| FROM | PA_OrfLibraries_V |
| WHERE | GeneCluID IN (SELECT GeneCluID |
|  | FROM PA_AccGeneClusters_V |
|  | WHERE Accession = 'A11530') |
|  | ORDER BY OrfID |

As described, Electronic Southerns are useful for identifying genomic libraries in which a given gene or ORF of interest exists. Some preferred and specific embodiments of the Electronic Southerns feature have been described. However, those of skill in the art will recognize that Electronic Southerns may be implemented in a database system according to the present invention in other ways which do not depart from the sprit and scope of the invention.

8. Conclusion

Although a few specific embodiments of the present invention have been described in detail, it should be understood that the present invention may be embodied in many other specific forms without departing from the spirit or scope of the invention as recited in the claims. For example, while the genomic database of this invention has been described as storing sequences of genomic nucleic acid along a contiguous sequence as the fundamental data unit, there is in principle no reason why other sequence units can not also be employed. For example, the databases of this invention could be employed to store and analyze expressed nucleic acid or amino acid sequences.

What is claimed is:

1. A method of comparing genetic complements of different types of organisms, the method comprising:
   providing a database including sequence libraries for a plurality of types of organisms, said libraries having multiple biomolecular sequences, at least some of which represent open reading frames located along one or more contiguous sequences on each of the plurality of organisms' genomes;
   receiving a selection of two or more of said sequence libraries for comparison;
   determining open reading frames common or unique to the selected sequence libraries; and
   displaying the results of said determination.

2. The method of claim 1, wherein the database includes biomolecular sequences from a microbial organism.

3. The method of claim 1 wherein the biomolecular sequences include nucleic acid sequences.

4. The method of claim 3, wherein the nucleic acid sequences include genomic sequences.

5. The method of claim 4, wherein the genomic sequences are microbial genomic sequences.

6. The method of claim 1, wherein the biomolecular sequences include peptide sequences.

7. The method of claim 1, wherein the step of receiving a selection of two or more of said sequence libraries for comparison includes receiving a user selection from two or more pull-down menus in a graphical user interface.

8. The method of claim 1, wherein the displaying step displays a unique identifier for a group of related opening reading frames.

9. The method of claim 8, wherein the display further comprises annotated information relating to the group of related open reading frames obtained from a public database.

10. The method of claim 1, wherein the open reading frames common to the selected libraries are determined and displayed.

11. The method of claim 1, wherein the open reading frames unique to a particular selected library are determined and displayed.

12. A method of comparing genomic complements of different types of organisms, the method comprising:
   providing a database including genomic libraries for a plurality of types of organisms, said libraries having multiple genomic sequences, at least some of which represent at least portions of open reading frames located along one or more contiguous sequences on each of the plurality of organisms' genomes;
   receiving a selection of two or more of said genomic libraries for comparison;
   determining sequences common or unique to the selected genomic libraries; and
   displaying the results of said determination.

13. The method of claim 12, wherein the genomic sequences are microbial genomic sequences.

14. The method of claim 12, wherein the step of receiving a selection of two or more of said sequence libraries for comparison includes receiving a user selection from two or more pull-down menus in a graphical user interface.

15. The method of claim 12, wherein the displaying step displays a unique identifier for a group of related opening reading frames.

16. The method of claim 15, wherein the display further comprises annotated information relating to the group of related opening reading frames obtained from a public database.

17. The method of claim 12, wherein said results are displayed as groupings of related open reading frames.

18. The method of claim 12, wherein the open reading frames common to the selected genomic libraries are determined and displayed.

19. The method of claim 12, wherein the open reading frames unique to a particular selected genomic library are determined and displayed.

20. A method of identifying genes common to a set of organisms, the method comprising:
   providing a database including genomic libraries for a plurality of types of organisms, said libraries having multiple genomic sequences, at least some of which represent open reading frames located along one or more contiguous sequences on each the plurality of organisms' genomes;
   displaying at least one list of said genomic libraries;
   receiving a user's selection of one or more genomic libraries from said at least one list;
   determining sequences common to the selected genomic libraries; and
   displaying the results of said determination.

21. The method of claim 20, wherein the displaying step displays a unique identifier for a group of related opening reading frames.

22. The method of claim 20, wherein the genomic sequences are microbial genomic sequences.

23. A method of identifying genes common to one or more in a set of organisms, the method comprising:
   providing a database including genomic libraries for a plurality of types of organisms, said libraries having multiple genomic sequences, at least some of which represent open reading frames located along one or more contiguous sequences on each the plurality of organisms' genomes;

displaying one or more lists of said genomic libraries;

receiving a user's selection of from none to all the genomic libraries from each of said lists;

determining sequences common to the selected genomic libraries from a first list or group of lists and absent in the genomic libraries of one or more other lists; and displaying the results of said determination.

24. The method of claim 23, wherein there are two lists of genomic libraries displayed.

25. The method of claim 23, wherein the second displaying step displays a unique identifier for a group of related opening reading frames.

26. The method of claim 23, wherein one library is selected from said first list or group of lists, and the remaining libraries are selected from said one or more other lists.

27. The method of claim 23, wherein the genomic sequences are microbial genomic sequences.

28. A computer system comprising:

a database including genomic libraries for a plurality of types of organisms, said libraries having multiple genomic sequences, at least some of which represent open reading frames located along one or more contiguous sequences on each the plurality of organisms' genomes; and a user interface capable of receiving a selection of two or more of said genomic libraries for comparison and displaying the results of said comparison.

29. The computer system of claim 28, wherein the genomic sequences are microbial genomic sequences.

30. A method of identifying libraries in which a given gene exists, the method comprising:

providing a database including genomic libraries for one or more types of organisms, said libraries having multiple genomic sequences, at least some of which represent open reading frames located along one or more contiguous sequences on each the one or more organisms' genomes;

receiving a selection of one or more probe sequences;

determining homologous matches between said probe sequences and the sequences in said genomic libraries; and displaying the results of said determination.

31. The method of claim 30, wherein said probe sequences and said library sequences are open reading frames.

32. The method of claim 30, wherein said results are displayed as groupings of related open reading frames.

33. The method of claim 30, wherein the genomic sequences are microbial genomic sequences.

34. A computer system, comprising:

a database including genomic libraries for one or more types of organisms, said libraries having multiple genomic sequences, at least some of which represent open reading frames located along one or more contiguous sequences on each the plurality of organisms' genomes;

a user interface capable of receiving a selection of one or more probe sequences for use in determining homologous matches between said one or more probe sequences and the sequences in said genomic libraries, and displaying the results of said determination.

35. The computer system of claim 34, wherein the genomic sequences are microbial genomic sequences.

36. A computer program product comprising a computer-usable medium having computer-readable program code embodied thereon relating to a database including genomic libraries for one or more types of organisms, said libraries having multiple genomic sequences, at least some of which represent open reading frames located along one or more contiguous sequences on each the one or more organisms' genomes, the computer program product comprising computer-readable program code for effecting the following steps within a computing system:

providing an interface for receiving a selection of two or more of said genomic libraries for comparison;

determining sequences common or unique to the selected genomic libraries; and displaying the results of said determination.

37. The computer program product of claim 36, wherein the sequences in said determining step are open reading frames.

38. The computer program product of claim 36, wherein the genomic sequences are microbial genomic sequences.

39. A computer program product comprising a computer-usable medium having computer-readable program code embodied thereon relating to a database including genomic libraries for one or more types of organisms, said libraries having multiple genomic sequences, at least some of which represent open reading frames located along one or more contiguous sequences on each the one or more organisms' genomes, the computer program product comprising computer-readable program code for effecting the following steps within a computing system:

providing an interface for receiving a selection of one or more probe open reading frames;

determining homologous matches between said probe sequences and the sequences in said genomic libraries; and displaying the results of said determination.

40. The computer program product of claim 39, wherein said probe and said library sequences in said determining step are open reading frames.

41. The computer program product of claim 39, wherein the genomic sequences are microbial genomic sequences.

42. A method of presenting the genetic complement of an organism, the method comprising:

providing a database including sequence libraries for a plurality of types of organisms, said libraries having multiple biomolecular sequences, at least some of which represent open reading frames located along one or more contiguous sequences on each of the plurality of organisms' genomes;

receiving a selection of one of said sequence libraries;

determining open reading frames within the selected sequence library; and displaying the results of said determination as one or more unique identifiers for groups of related opening reading frames.

43. The method of claim 42, wherein the display further comprises annotated information relating to the group of related opening reading frames obtained from a public database.

44. The method of claim 42, wherein the genomic sequences are microbial genomic sequences.

* * * * *